(12) United States Patent
Ripoll Lorenzo et al.

(10) Patent No.: US 8,170,651 B2
(45) Date of Patent: May 1, 2012

(54) IMAGING VOLUMES WITH ARBITRARY GEOMETRIES IN NON-CONTACT TOMOGRAPHY

(75) Inventors: Jorge Ripoll Lorenzo, Madrid (ES); Vasilis Ntziachristos, Cambridge, MA (US); Karen Madden, Sudbury, MA (US)

(73) Assignee: VisEn Medical, Inc., Woburn, MA (US)

( * ) Notice: Subject to any disclaimer, the term of this patent is extended or adjusted under 35 U.S.C. 154(b) by 0 days.

(21) Appl. No.: 12/688,661

(22) Filed: Jan. 15, 2010

(65) Prior Publication Data

US 2010/0292567 A1 Nov. 18, 2010

Related U.S. Application Data

(63) Continuation of application No. 11/003,936, filed on Dec. 3, 2004, now abandoned, which is a continuation of application No. PCT/US03/17558, filed on Jun. 4, 2003.

(60) Provisional application No. 60/385,931, filed on Jun. 4, 2002.

(51) Int. Cl.
*A61B 6/00* (2006.01)

(52) U.S. Cl. ........ 600/476; 600/407; 600/473; 600/474; 600/475; 600/477

(58) Field of Classification Search .................. 600/407, 600/473–478
See application file for complete search history.

(56) References Cited

U.S. PATENT DOCUMENTS

| | | | |
|---|---|---|---|
| 4,281,645 A | 8/1981 | Jobsis | |
| 4,321,930 A | 3/1982 | Jobsis et al. | |
| 4,920,491 A | 4/1990 | Eberhard et al. | |
| 5,070,455 A | 12/1991 | Singer et al. | |
| 5,090,415 A | 2/1992 | Yamashita et al. | |
| 5,391,877 A | 2/1995 | Marks | |
| 5,640,247 A | 6/1997 | Tsuchiya et al. | |
| 5,699,798 A | 12/1997 | Hochman et al. | |
| 5,762,607 A | 6/1998 | Schotland et al. | |
| 5,827,190 A | 10/1998 | Palcic et al. | |
| 5,865,754 A | 2/1999 | Sevick-Muraca et al. | |
| 6,026,319 A | 2/2000 | Hayashi et al. | |

(Continued)

FOREIGN PATENT DOCUMENTS

DE 4445214 6/1996

(Continued)

OTHER PUBLICATIONS

Ripoll, J. et al., "Boundary conditions for Light Propagation in Diffussive Media with Nonscattering Regions", Journal of the Optical Society of America A, 17(9);1671-1681 (Sep. 2000).*

(Continued)

*Primary Examiner* — Brian Casler
*Assistant Examiner* — Joseph M Santos
(74) *Attorney, Agent, or Firm* — Goodwin Proctor LLP

(57) ABSTRACT

A method for tomographic imaging of diffuse medium includes directing waves into a diffusive medium, solving a surface-bounded inversion problem by forward field calculations through decomposition of contributions from the multiple reflections from an arbitrary surface within the diffusive medium or outside the diffusive medium into a sum of different orders of reflection up to an arbitrary order, and using contact or non-contact measurements of waves outside said diffusive medium to generate a tomographic image.

13 Claims, 15 Drawing Sheets

U.S. PATENT DOCUMENTS

| | | | |
|---|---|---|---|
| 6,075,610 | A | 6/2000 | Ueda et al. |
| 6,081,322 | A | 6/2000 | Barbour |
| 6,205,347 | B1 | 3/2001 | Morgan et al. |
| 6,205,353 | B1 * | 3/2001 | Alfano et al. ............ 600/476 |
| 6,219,279 | B1 | 4/2001 | Manolescu et al. |
| 6,304,771 | B1 * | 10/2001 | Yodh et al. ............ 600/476 |
| 6,377,841 | B1 | 4/2002 | Lin et al. |
| 6,377,842 | B1 | 4/2002 | Pogue et al. |
| 6,526,309 | B1 | 2/2003 | Chance |
| 6,615,063 | B1 * | 9/2003 | Ntziachristos et al. ....... 600/312 |
| 6,825,928 | B2 | 11/2004 | Liu et al. |
| 7,383,076 | B2 | 6/2008 | Ntziachristos et al. |
| 7,647,091 | B2 | 1/2010 | Ntziachristos et al. |
| 2004/0015062 | A1 | 1/2004 | Ntziachristos et al. |
| 2004/0021771 | A1 | 2/2004 | Stearns et al. |
| 2005/0149877 | A1 | 7/2005 | Rice et al. |
| 2005/0283071 | A1 * | 12/2005 | Ripoll et al. ............ 600/425 |
| 2007/0238957 | A1 | 10/2007 | Yared |
| 2008/0219933 | A1 | 9/2008 | Ntziachristos et al. |
| 2008/0312540 | A1 | 12/2008 | Ntziachristos |

FOREIGN PATENT DOCUMENTS

| | | |
|---|---|---|
| EP | 0329115 | 8/1989 |
| EP | 0559978 | 9/1993 |
| EP | 0905509 | 3/1999 |
| EP | 1018747 | 7/2000 |
| JP | 04-122248 | 4/1992 |
| JP | 05-223738 | 8/1993 |
| JP | 08-131445 | 5/1996 |
| JP | 11-173976 | 7/1999 |
| WO | WO-99/20997 | 4/1999 |
| WO | WO-02/41760 | 5/2002 |
| WO | WO-03/102558 A1 | 12/2003 |
| WO | WO-2004/072906 A1 | 8/2004 |
| WO | WO-2009/009178 | 1/2009 |
| WO | WO-2009/055095 | 4/2009 |

OTHER PUBLICATIONS

Macaskill, C. et al., "Iterative Approach for the Numerical Simulation of Scattering frome one- and two- Dimensional Rough Surfaces", Applied Optics, 32(15);2839-2847 (May 20, 1993).*

Aronson, R., (1995) "Boundary conditions for diffusion of light," J. Opt. Soc. Am. A 12, 2532-2539. cited by other.

Graves et al. (2003), "A Submillimeter Resolution Fluorescence Molecular Imaging System for Small Animal Imaging," 2003 Amer. Assoc. Med. Phys. 30(5): May 2003; 901-911. cited by other.

Boas, D.A. et al., "Scattering and Imaging with Diffusing Temporal Field Correlations," Physical Review Letters, 76(0); 1855-1858 (Aug. 28, 1995).

Li, X. D., T. Durduran, et al. (1997) "Diffraction tomography for biochemical imaging with diffuse-photon density waves." Optics Letters 22: 573-575. cited by other.

Li, X., D. N. Pattanayak, et al. (2000). "Near-field diffraction tomography with diffuse photon density waves." Phys Rev E 61(4 Pt B): 4295-309. cited by other.

Macaskill et al.; "Iterative Approach for the Numerical Simulation of Scattering from One- and Two-Dimensional Rough Surfaces," 1993 Optical Society of America, Applied Optics, vol. 32, No. 15; May 20, 1993; pp. 2839-2847. cited by other.

Markel, V. A. and J. C. Schotland (2001) "Inverse problem in optical diffusion tomography. I. Fourier-Laplace inversion formulas." J Opt Soc Am A Opt Image Sci Vis 18(6): 1336-47. cited by other.

Markel, V. A. and J. C. Schotland (2001) "Inverse scattering for the diffusion equation with general boundary conditions." Phys Rev E 64(3 Pt 2): 035601: 1-4. cited by other.

Markel, V. A. and J. C. Schotland (2004) "Symmetries, inversion formulas, and image reconstruction for optical tomography." Phys Rev E Stat Nonlin Soft Matter Phys 70(5 Pt 2): 056616: 1-19. cited by other.

Matson, C. L. (2002) "Diffraction Tomography for Turbid Media." Advances in Imaging and Electron Physics 124: 253-342. cited by other.

Matson, C. L., N. Clark, et al. (1997) "Three-dimensional tumor localization in thick tissue with the use of diffuse photon-density waves." Applied Optics 36: 214-220. cited by other.

Ntziachristos et al.; "Experimental Three-Dimensional Fluorescence Reconstruction of Diffuse Media by use of a Normalized Born Approximation," 2001 Optical Society of America, Optics Letters, vol. 26, No. 12; Jun. 15, 2001; pp. 893-895. cited byother.

PCT International Preliminary Examination Report for PCT Pat. App. No. PCT/US01/44764, dated Dec. 21, 2002, 3 sheets. cited by other.

PCT International Preliminary Examination Report for PCT Pat. App. No. PCT/US03/17558, dated Jul. 8, 2005, 3 sheets. cited by other.

PCT International Search Report for PCT Pat. App. No. PCT/US01/44764, dated Nov. 13, 2002, 1 sheet. cited by other.

PCT International Search Report for PCT Pat. App. No. PCT/US03/17558, mailed Nov. 6, 2003, 3 sheets. cited by other.

PCT Search Report and Written Opinion of the ISA for PCT/US2004/003229 dated Aug. 9, 2004. cited by other.

Ripoll and Ntziachristos (2006) "From Finite to Infinite Volumes: Removal of Boundaries in Diffuse Wave Imaging", Physical Review Letters 96, 173903: 1-4. cited by other.

Ripoll et al.; "Boundary Conditions for Light Propagation in Diffusive Media with Nonscattering Regions," Journal of the Optical Society of America A; vol. 17, No. 9; Sep. 2000; pp. 1671-1681. cited by other.

Ripoll, J. and M. Nieto-Vesperinas, (1999) "Scattering integral equations for diffusive waves: detection of objects buried in diffusive media in the presence of rough interfaces," J. Opt. Soc. Am. A 16, 1453-1465. cited by other.

Ripoll, J. and V. Ntziachristos (2003) "Iterative boundary method for diffuse optical tomography." J. Opt. Soc. Am. A 20(6): 1103-1110. cited by other.

Ripoll, J., D. Yessayan, et al. (2005) "Experimental determination of photon propagation in highly absorbing and scattering media." J. Opt. Soc. Am. A 22(3):546-551. cited by other.

Ripoll, J., M. Nieto-Vesperinas, et al. (1999) "Spatial resolution of diffuse photon density waves." J. Opt. Soc. Am. A 16: 1466-1476. cited by other.

Ripoll, J., V. Ntziachristos, et al. (2001) "The Kirchhoff Approximation for diffusive waves." Phys. Rev. E 64: 051917: 1-8. cited by other.

Schotland, J. C. and V. A. Markel (2001) "Inverse scattering with diffusing waves." J Opt Soc Am A Opt Image Sci Vis 18(11): 2767-77. cited by other.

Ripoll, J. et al., "Reflection and Transmission Coefficients for Diffuse Photon Density Waves," Optics Letters, 24(12):796-798 (Jun. 15, 1999).

Ntziachristos, V. et al., "Concurrent MRI and Diffuse Optical Tomography of Breast After Indocyanine Green Enhancement," PNAS, 97(6):2767-2772 (Mar. 14, 2000).

Ntziachristos, V. et al., "Would Near-Infrared Fluorescence Signals Propagate Through Large Human Organs for Clinical Studies?," Optics Letters, 27(5)333-335 (Mar. 1, 2002).

Yaghjian, A.D., "Electric Dyadic Green's Functions in the Source Region," Proceedings of the IEEE, 68(2):248-263 (Feb. 1980).

U.S. Appl. No. 60/445,016, filed Feb. 5, 2003, 45 pages.

* cited by examiner

IMAGING VOLUMES WITH ARBITRARY GEOMETRIES IN NON-CONTACT TOMOGRAPHY

RELATED APPLICATIONS

This application is a continuation of U.S. patent application Ser. No. 11/003,936, filed Dec. 3, 2004, abandoned, which is a continuation of International Application No. PCT/US03/17558, which designated the United States and was filed on Jun. 4, 2003, published in English, on Dec. 11, 2003, as International Publication Number WO 2003/102558, which claims the benefit of U.S. Provisional Application No. 60/385,931, filed on Jun. 4, 2002. The entire teachings of the above applications are incorporated herein by reference.

BACKGROUND OF THE INVENTION

Optical imaging is an evolving clinical imaging modality that uses penetrating lights rays to create images of both intrinsic and extrinsic biological scatterers. Light offers unique contrast mechanisms that can be based on absorption, e.g., probing of hemoglobin concentration or blood saturation, and/or fluorescence, e.g., probing for weak auto-fluorescence, or exogenously administered fluorescent probes (Neri et al., *Nat. Biotech.* 15:1271-1275, 1997; Ballou et al., *Cancer Immunol. Immunother.* 41:257-63,1995; and Weissleder, et al., *Nat. Biotech.* 17:375-178, 1999). Preferably, light in the red and near infrared range (600-1200 nm) is used to maximize tissue penetration and minimize absorption from natural biological absorbers such as hemoglobin and water. (Wyatt, *Phil. Trans. R. Soc. London B* 352:701-706, 1997; Tromberg, et al., *Phil. Trans. R. Soc. London B* 352:661-667, 1997).

Diffuse optical tomography (DOT) is one type of optical tomography that has been used for quantitative, three-dimensional imaging of biological tissue, based on intrinsic absorption and scattering. (Ntziachristos et al., *Proc. Natl. Acad. Sci. USA*, 97:2767-72, 2000; Benaron et al., *J. Cerebral Blood Flow Metabol.* 20:469-77, 2000) A typical DOT imaging system uses narrow-band light sources so that specific extrinsic and/or intrinsic fluorophores are targeted. Light, customarily generated by laser diodes, is usually directed to and from the target tissue using fiber guides, since (1) it enables flexibility in the geometrical set-up used, (2) reduces signal loss, and (3) simplifies the theoretical modeling of contact measurements. The use of fiber guides, however, has significant disadvantages. The most significant is that only a limited number of detector channels can be implemented since scaling up requires a large number of fibers (usually fiber bundles) that have to be coupled to the tissue, which in many cases is not practical. In addition, it is also very difficult to control or measure the exact coupling conditions of each individual fiber or fiber bundle, which can vary quite significantly from fiber to fiber. An alternative to fibers is to use a compression plate and/or an optical matching fluid. For example, it is common to compress the tissue of investigation into a fixed geometry such as a slab or circle and to use an optical matching fluid to eliminate possible air-tissue interfaces. In either case, the use of fiber guides and/or optical matching fluids and fixed geometries impedes the experimental practicality and severely limits the tomographic capacity of the imaging system. These constraints result in significant limitations to the use of these systems either in research or in the clinic. To date, non-contact systems and methods for tomography of biological tissue and other diffuse and diffuse-like medium with arbitrary boundaries have not been developed or reported.

Currently, optical tomography utilizes either numerical or analytical methods for solving the equations governing propagation of light through biological tissue. Numerical methods, such as the finite element method (FEM), finite differences (FD) or the boundary element method (BEM), are used for complex geometries of air/tissue boundaries and are extremely computationally costly and therefore are currently non-viable in a real-time three-dimensional research and clinical setting. (For example, reported numerical-based reconstruction times for a simulated typical 3D breast-imaging problem on state of the art single processor computers range from 6 to 36 hours.) Analytical methods are much faster (for example, an analytical-based 3D reconstruction case of the breast ranges between 2-15 minutes), but are available only for simple geometries of air/tissue boundary such as a slab, a cylinder or a sphere, and often lack adequate accuracy for imaging complex objects such as a human breast.

An alternative method to perform tomography of diffuse or diffuse-like medium with complex geometries is by means of an analytical approach called the Kirchhoff Approximation (KA). This method uses the angular spectrum representation of the propagating average intensity and employs the reflection coefficients for light waves to calculate the light intensity inside any arbitrary geometry. Although in contact imaging applications the KA can achieve relatively good computational efficiency (Ripoll et al., *Opt. Lett.* 27:333-335, 2002), it has several significant limitations that would restrict its use in real research and clinical settings. Specifically, the KA is limited to geometries such as a cylinder or ellipse, i.e. geometries that do not include shadow regions. Furthermore, the KA method generally works for larger volumes (e.g., diameters >3 cm), and for highly absorbing medium (e.g., typically the absorption coefficient must be 10-100 times higher than that of water).

SUMMARY OF THE INVENTION

There is a need for fast computational methods for real-time optical tomo graphic diagnostics and other research and clinical uses that can deal with arbitrary sizes, shapes and boundaries that (1) attain the computational simplicity and efficiency of analytical methods while (2) retaining the accuracy and capacity of numerical methods to model arbitrary shapes and boundaries, and (3) can be applied both to contact and non-contact measurements of diffuse and diffuse-like medium.

The invention is directed to an imaging system and a method for imaging volumes or subjects containing interfaces such as diffuse and non-diffuse tissue interfaces or other interfaces using analytical methods.

In one embodiment, the present invention is a method for tomographic imaging of diffuse medium comprising directing waves into a medium having a boundary S, detecting an intensity of waves emitted from the medium by using contact or non-contact measurements of waves outside the medium, and processing the detected intensity to generate a tomographic image.

In another embodiment, the present invention is a method of obtaining a tomographic image of a target region within an object, the method comprising directing light waves from multiple points into an object, detecting light waves emitted from multiple points from the object, wherein the light is emitted from an intrinsic absorber, fluorochrome, or scatterer, processing the detected light by representing the contribution of each wave into the detected intensity as a sum of an arbitrary number N of terms in a series and wherein each term in the series is an intensity of a wave reflected from an arbitrary surface within or outside a diffusive medium, and forming a tomographic image that corresponds to a three-dimensional target region within said object and to a quantity of intrinsic absorber, fluorochrome, or scatterer in the target region.

In another embodiment, the present invention is a method of obtaining a tomographic image of a target region within an object comprising administering to an object a fluorescent imaging probe, directing light waves from multiple points into the object, detecting fluorescent light emitted from multiple points from the object, processing the detected light by representing the contribution of each wave into the detected intensity as a sum of an arbitrary number N of terms in a series and wherein each term in the series is an intensity of a wave reflected from an arbitrary surface within or outside a diffusive medium, and forming a tomographic image that corresponds to a three-dimensional target region within the object and to a quantity of fluorescent imaging probe in the target region.

In another embodiment, the present invention is a tomographic imaging system comprising a wave source block to direct waves into an object, a wave detector block to detect the intensity of waves emitted from the object and to convert the intensity of the waves into a digital signal representing waves emitted from the object, a processor to control the detector block and, optionally, the source block and to process the digital signal representing waves emitted from the object into a tomographic image on an output device, wherein the processor is programmed to process the digital signal by representing the contribution of each wave into the detected intensity as a sum of an arbitrary integer number N of terms in a series and wherein each term in the series is an intensity of a wave reflected from an arbitrary surface within or outside a medium.

In another embodiment, the present invention is an apparatus comprising machine executable code for a method of tomographic imaging of medium including directing waves into a medium having a boundary S, detecting an intensity of waves emitted from the medium by using contact or non-contact measurements of waves outside the medium, processing the detected intensity to generate a tomographic image by representing the contribution of each wave into the detected intensity as a sum of an arbitrary integer number N of terms in a series and wherein each term in the series is an intensity of a wave reflected from an arbitrary surface within or outside the medium.

The approach described herein provide several advantages over the existing art, including (1) the ability to image volumes with 2D or 3D geometries of arbitrary size, shape and boundaries using fast and accurate analytical methods, and (2) the application of these new methods for both contact and non-contact tomography of diffuse and diffuse-like medium. These new imaging methods can have broad applications in a wide variety of areas in research and clinical imaging. Importantly, these methods significantly improve existing tomographic imaging techniques and make possible the use of these imaging techniques in real-time animal and human subject imaging and clinical medical diagnostics by allowing the implementation of practical systems with unprecedented capacity for data collection.

Furthermore, the approach described herein can be applied both to contact and non-contact measurements, as well as for any diffuse and non-diffuse interfaces as related to tomography, including optical tomography, fluorescence-mediated tomography, near-field optical tomography, tomography with thermal waves and generally any surface-bounded inversion problems of tissues and other diffuse or diffuse-like medium.

BRIEF DESCRIPTION OF THE DRAWINGS

The foregoing and other objects, features and advantages of the invention will be apparent from the following more particular description of preferred embodiments of the invention, as illustrated in the accompanying drawings. The drawings are not necessarily to scale, emphasis instead being placed upon illustrating the principles of the invention.

DETAILED DESCRIPTION OF THE INVENTION

Figure 1:
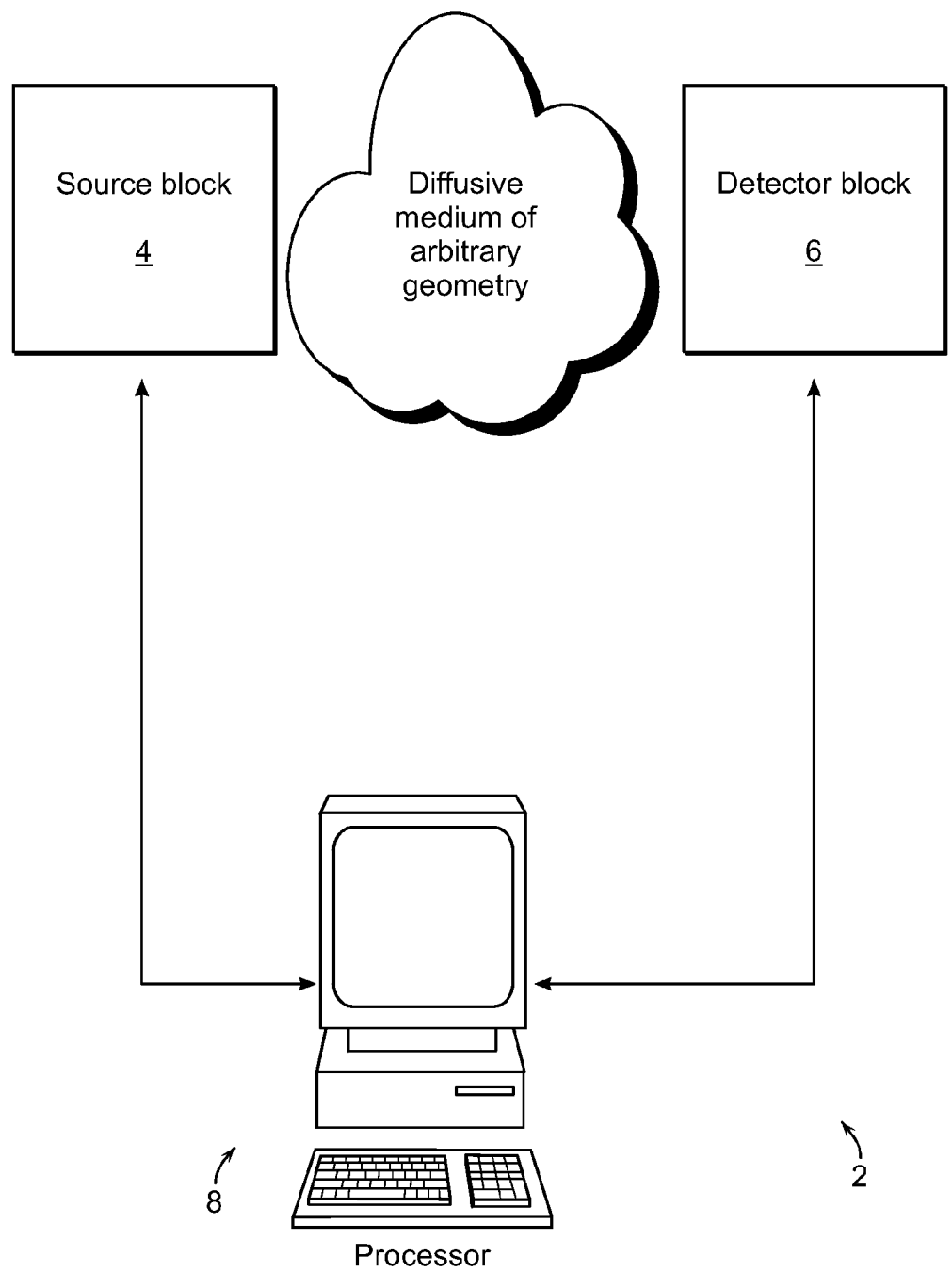
FIG. 1 is a block-diagram of a preferred embodiment of a system of the present invention.

The purpose of optical tomography is to recover the optical properties, location, and shape of objects buried deep inside a specific volume by solving equations that describe light propagation through diffuse medium, such as biological tissue. As used herein, the terms "diffuse medium" or "diffusive medium" are used interchangeably and are defined to mean media where waves suffer multiple scattering events with small particles (the scatterers) within an otherwise homogeneous medium, randomizing their phase; in this case it is the average wave intensity that is studied. The average wave intensity will follow the diffusion equation, behaving in itself as a "diffuse wave" and interacting with surfaces and boundaries. The terms "non-diffuse medium" or "non-diffusive medium" are used interchangeably and are defined to mean media where waves do not suffer multiple scattering events with scatterers within the medium and maintain their phase; within these media, waves will interact and suffer multiple scattering events with surfaces and boundaries. Analytical solutions are available only for a small number of simple geometries of the air/tissue boundaries, such as cylinders, spheres, and slabs. Due to the lack of an appropriate theoretical method for more complex boundaries, numerical methods need to be used. Numerical methods offer practical simplicity but also significant computational burden, especially when large three-dimensional reconstructions are involved. Such methods include the finite element method (FEM), finite differences (FD), and the extinction theorem (ET) or Boundary Element Method (BEM).

Generally, optical tomographic analysis is divided into two steps. The first step is solving the "forward problem," in which a solution of the wave transport or "diffusion" equation, is used to describe the wave propagation through a medium with assumed optical or other wave-transmitting properties, e.g., tissue, and is used to predict the intensity of light detected emerging from this medium. In a preferred embodiment, the "diffusion equation" is $$\nabla \{D \nabla U\} + \frac{1}{c} \frac{\partial U}{\partial t} - \mu_a U = S,$$

where D is the diffusion coefficient which may be time, frequency, absorption, scattering and/or spatially-dependent, c is the speed of light in the medium, U is the average intensity or the energy density, $\mu_a$ is the absorption coefficient, and S is the source function which represents the intensity and flux distribution within the medium. As used herein, the terms "average intensity" and "energy density" can be used interchangeably, as can be the terms "flux" and "fluence". The second step is solving the "inverse problem," in which the optical or other wave-transmitting properties of the medium are updated to minimize the errors observed between the predicted and measured fields.

There are several ways to solve the forward problem (by obtaining analytical and numerical solutions of the diffusion equation) and inverse problem (direct inversion, $\chi^2$-based fits, and algebraic reconstruction techniques).

An embodiment of the invention is a tomographic imaging system 2 depicted in FIG. 1. The tomographic imaging system includes a wave source block 4 to direct waves into an object; a wave detector block 6 to detect the intensity of waves emitted from the object and to convert the intensity of the waves into a digital signal representing waves emitted from the object; and a processor 8 to control the detector block and, optionally, the source block and to process the digital signal representing waves emitted from the object into a tomographic image on an output device. The processor is programmed to process the digital signal by representing the contribution of each wave into the detected intensity as a sum of an arbitrary integer number N of terms in a series and wherein each term in the series is an intensity of a wave reflected from an arbitrary surface within or outside the medium.

In another embodiment, the present invention is an apparatus comprising machine executable code for a method of tomographic imaging of medium including the steps of directing waves into a medium having a boundary S; detecting an intensity of waves emitted from the medium by using contact or non-contact measurements of waves outside the medium; and processing the detected intensity to generate a tomographic image by representing the contribution of each wave into the detected intensity as a sum of an arbitrary integer number N of terms in a series and wherein each term in the series is an intensity of a wave reflected from an arbitrary surface within or outside the medium.

Without being limited to any particular theory, it is believed that the physical foundation of the method of the present invention is as set forth below.

Green's Function

Figure 2:
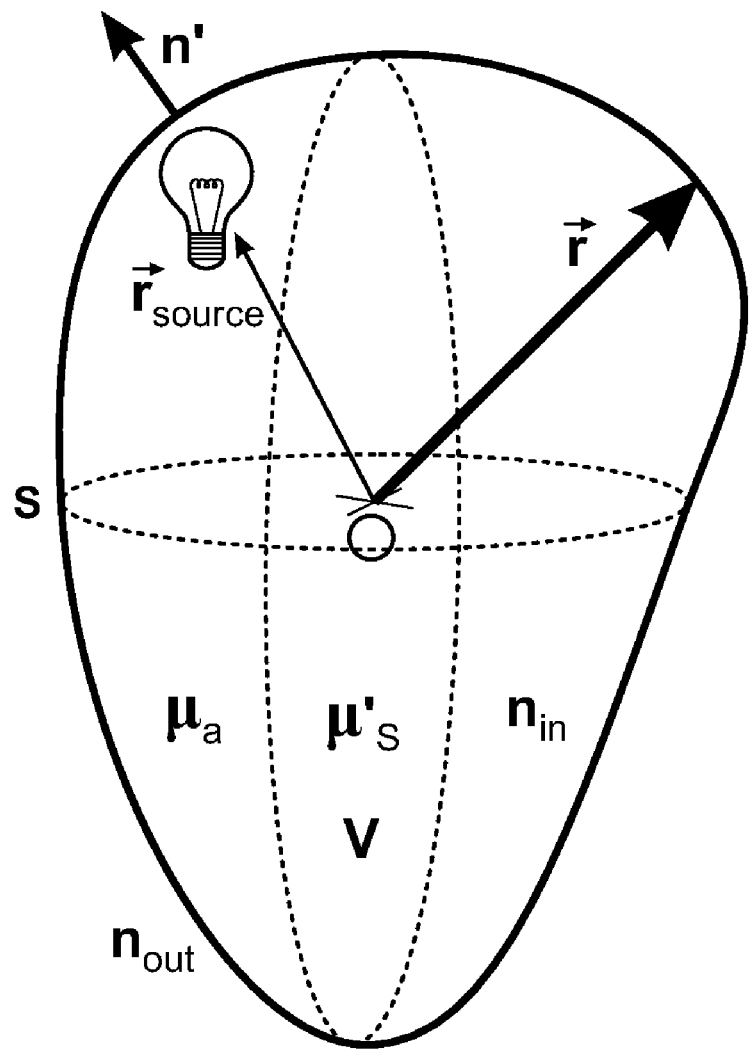
FIG. 2 shows a surface-bounded volume of arbitrary geometry. An optically diffuse volume V is surrounded by a boundary surface S of arbitrary two-dimensional or three-dimensional shape. The volume is illuminated at position $r_{source}$.

FIG. 2 illustrates a general imaging model where there is a diffusive volume V delimited by surface S, which can be imaged. This diffusive medium is characterized by its absorption coefficient $\mu_a$, the diffusion coefficient D, and the refractive index $n_{in}$ and is surrounded by a non-diffusive medium of refractive index $n_{out}$. Generally, any time-dependent fluctuation of the average intensity U at any point in space r can be expressed in terms of its frequency components through its Fourier transform as:

$$U(r,t) = \int_{-\infty}^{+\infty} U(r,\omega) \exp[-i\omega t] d\omega \quad (1)$$

If in such a medium the light source is modulated at a single frequency $\omega$, the average intensity is:

$$U(r,t) = U(r,\omega) \exp[-i\omega t] \quad (2)$$

Function U(r, t) in Eq. (2) and the functions U(r,ω) in Eq. (1) represent diffuse photon density waves (DPDW) (Boas et al, (1995) *Phys. Rev. Lett.* 75:1855-1858, the entire teachings of which are incorporated herein by reference) and obeys the Helmholtz equation with a wave number $\kappa = (-\mu_a/D + i\omega/cD)^{1/2}$, where c is the speed of light in the medium. The unknown function U(r, t) can be obtained if a so-called Green function that models light propagation within the medium from a point source to a point detector is known. Since all regimes: CW, frequency domain, and time-domain, can be expressed in terms of Eq. (1), all expressions will be derived in the frequency domain without loss of generality, and in most cases a time or frequency dependence will be assumed and not included implicitly.

In an infinite geometry (no air/time boundary), the so-called homogenous Green's function g(r) is obtained by solving Eq. (3):

$$\nabla^2 g(\kappa|r_s - r_d|) + \kappa^2 g(\kappa|r_s - r_d|) = -\frac{4\pi}{D} \delta(r_s - r_d), \quad (3)$$

written here in the frequency domain (omitting time- and/or frequency dependent terms). $r_s$ is the position of the source, $r_d$ is the position of the detector, $\nabla^2$ denotes the Laplacian operator $$\nabla^2 = \frac{\partial^2}{\partial x^2} + \frac{\partial^2}{\partial y^2} + \frac{\partial^2}{\partial z^2},$$

and $\delta(r_s - r_d)$ is the Dirac's delta-function (G. B. Arfken and H. J. Weber, Mathematical Methods for Physicists (Academic Press, New York, 1995). The solution of (3) in 3D is given by Eq. (4):

$$g(\kappa|r_s - r_d|) = \frac{\exp[i\kappa|r_s - r_d|]}{D|r_s - r_d|}. \quad (4)$$

Considering the geometry of the problem, a complete Green's function $G(r_s, r_d)$ can be defined, which models propagation of the diffuse photon waves from a point source to a point detector inside an arbitrarily shaped diffusive volume taking into account all boundaries present. By means of this complete Green's function the average intensity at a point $r_d$ inside the medium is defined as:

$$U(r_d) = \frac{1}{4\pi} \int_V S(r')G(r', r_d)\,dr', \quad (5)$$

$$r_d \in V$$

where S(r') is the source term (i.e., the strength of the light source at position r' given in units of energy density), and V is the volume occupied by the diffusive medium.

In infinite space the equation is $G(r_s,r_d)=g(\kappa|r_s-r_d|)$. Preferably, the source and detector are both inside the volume V.

For a homogeneous diffusive volume limited by surface S, i.e., a volume of spatially invariant absorption and scattering coefficients inside S, the solution to Eq. (5) for arbitrary geometries of S can be expressed in terms of a surface integral by means of Green's Theorem (Ripoll et al, *J. Opt. Soc. Am. A* 17:1671-1681, 2000 the entire teachings of which are incorporated herein by reference) as:

$$G(r_s, r_d) = g(\kappa|r_s - r_d|) - \quad (6)$$

$$\frac{1}{4\pi}\int_S \left[ G(r_s, r') \frac{\partial g(\kappa|r' - r_d|)}{\partial n'} - g(\kappa|r' - r_d|) \frac{\partial G(r_s, r')}{\partial n'} \right] dS',$$

where n is the surface normal pointing into the non-diffusive medium. The boundary condition between the diffusive and non-diffusive medium (Aronson, J. Opt. Soc. Am. A 16 (5): 1066-1071, 1999; Aronson R, *J. Opt. Soc. Am. A* 12, 2532 1995; Ishimaru A., Wave Propagation and Scattering in Random Media, New York: IEEE press 1997) is:

$$G(r_s,r')|_S = -C_{nd}Dn\cdot\nabla G(r_s,r')|_S, r'\in S \quad (7)$$

Introducing Eq. (7) into Eq. (6) we obtain:

$$G(r_s, r_d) = g(\kappa|r_s - r_d|) + \quad (8)$$

$$\frac{1}{4\pi}\int_S \left[ C_{nd}D\frac{\partial g(\kappa|r' - r_d|)}{\partial \hat{n}'} + g(\kappa|r' - r_d|) \right]\frac{\partial G(r_s, r')}{\partial \hat{n}'} dS'.$$

where $C_{nd}$ is a total reflectivity of the boundary surface S, integrated over all angles, and expressed through the Fresnel reflection coefficients r as:

$$C_{nd} = \frac{2 - R_J^{1\to 0} - R_J^{0\to 1}}{R_U^{0\to 1}}$$

where $$R_J^{1\to 0} = \int_0^1 [1-|r_{10}(\mu)|^2]\mu^2 d\mu$$

$$R_J^{0\to 1} = \int_0^1 [1-|r_{01}(\mu)|^2]J\mu d\mu$$

$$R_U^{0\to 1} = \int_0^1 [1-|r_{01}(\mu)|^2]\mu^2 d\mu$$

and where $\mu=\cos\theta$ for an incidence angle $\theta$, $r_{01}$ and $r_{10}$ represent the reflection coefficients when the incident wave comes from the inner, diffusive medium having an index of refraction $n_{in}$, or outer, non-diffusive medium having an index of refraction $n_{out}$, respectively, and are defined in terms of the parallel and perpendicular polarization components as:

$$|r|^2 = \frac{1}{2}(|r_\perp|^2 + |r_\parallel|^2),$$

$$r_\perp = \frac{n_{in}\cos\theta_t - n_{out}\cos\theta_i}{n_{in}\cos\theta_t + n_{out}\cos\theta_i},$$

$$r_\parallel = \frac{n_{in}\cos\theta_i - n_{out}\cos\theta_t}{n_{in}\cos\theta_i + n_{out}\cos\theta_t},$$

and where $\cos\theta_t$ is the cosine of the transmitted angle, which is found from Snell's law $n_{out}\sin\theta_t=n_{in}\sin\theta_i$. In Eq. (8) D is the medium's diffusion coefficient, where n is the unity vector normal to surface S and pointing into the non-diffusive medium, and $\kappa$, $r_s$, and $r_d$ are defined above for Eq. (4). Eq. (8) is an integral equation that defines the complete Green function $G(r_s, r_d)$. Substituting a known function $G(r_s, r_d)$ into Eq. (5) allows the average intensity at a point $r_d$ inside the medium $U(r_d)$ to be calculated for a given frequency $\omega$, which, in turn, allows the value of the average intensity of light at point r at time t, U(r, t) represented by Eq. (1) to be calculated.

Kirchhoff Approximation and its Application to Solving the Forward Problem

When many solutions to a forward problem need to be generated, such as in iterative reconstruction schemes, a first-order approximation to Eq. (8), applicable to arbitrary geometries in 3D is needed, both for the sake of computing time and memory. One such approximation applicable to arbitrary geometries is the Kirchhoff Approximation (KA), sometimes also known as the physical-optics or the tangent-plane method (Ogilvy, London, IOP publishing, 1991; Nieto-Vesperinas, Pergamon, New York, 1996 the entire teachings of which are incorporated herein by reference), so long as the curvature of the surface under study is larger than the wavelength. The KA therefore only considers first order reflections at an interface decomposed into planar components and in the case of a planar surface yields exact solutions.

For diffusive point sources, the Kirchhoff Approximation (KA) assumes that the surface is replaced at each point by its tangent plane. Referring to FIG. 3(a), where $R_s$ is the position of the source and $r_p$ is an arbitrary point on the surface, the total average intensity U at any point $r_p$ of the surface S is given by the sum of the homogeneous incident intensity $U^{inc}$ and that of the wave reflected from the local plane of normal $n(r_p)$. In terms of the Green's function this is expressed as:

$$G^{KA}(r_s,r_p)=g(\kappa|r_s-r_p|)*[1+R_{ND}], \quad (9)$$

where * denotes convolution:

$$g(r_s, r_p)*[1 + R_{ND}(r_p)] = \int_{-\infty}^{+\infty} \left[\begin{array}{c}\delta(r' - r_p) + \\ R_{ND}(r' - r_p)\end{array}\right]g(r_s, r')dr'$$

and $R_{ND}$ is the reflection coefficient for diffusive waves defined in Fourier space as (J. Ripoll et al, *J. Opt. Soc. Am. A* 18, 2001):

$$R_{ND}(K) = \frac{iC_{nd}D\sqrt{\kappa^2 - K^2} + 1}{iC_{nd}D\sqrt{\kappa^2 - K^2} - 1}. \quad (10)$$

$g(\kappa|r_s-r_d|)$ is defined by equation (4), $\kappa$, $r_s$, and $r_d$ are defined above for Eq. (3), $C_{nd}$ is defined above for Eq. (7) and (8), and K is the spatial variable in the R=(x,y) plane in the Fourier domain (spatial frequency): $R_{ND}(K)=\int_{-\infty}^{+\infty}R_{ND}(R)\exp[iK\cdot R]dR$.

Taking into consideration the different propagation directions of the incident and reflected wave with respect to the local plane, the gradient of the Green's function is:

$$\frac{\partial G^{KA}(r_s, r_p)}{\partial \hat{n}_p} = \frac{\partial g(\kappa|r_s - r_p|)}{\partial \hat{n}_p} * [1 - R_{ND}], \quad (11)$$

Figure 3B:
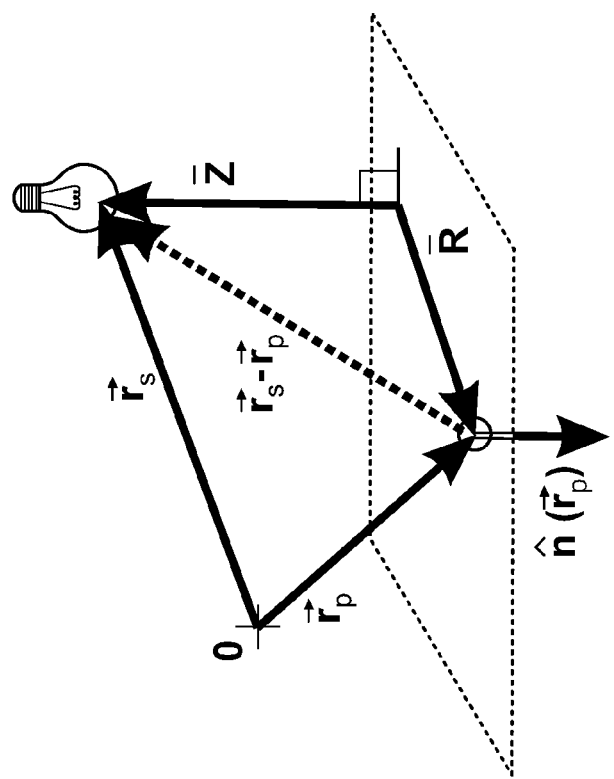
FIG. 3(b) shows KA representation in the coordinates of the tangent plane.
Figure 3A:
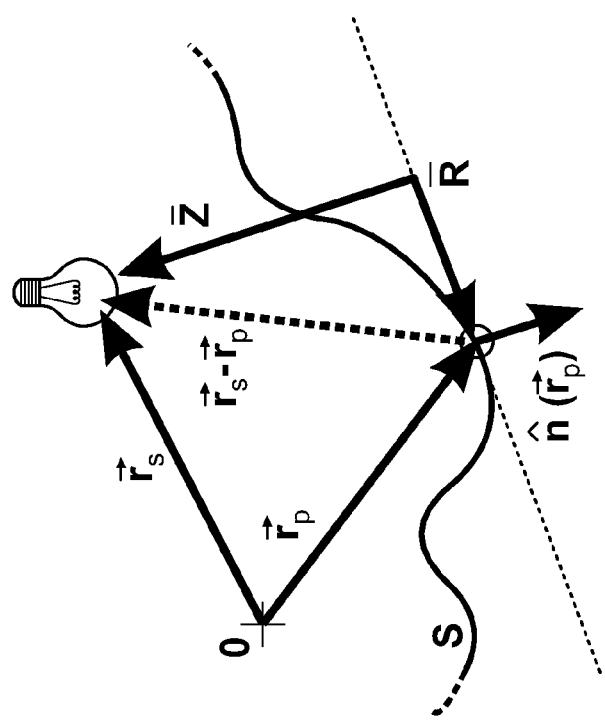
FIG. 3(a) shows a vector representation at the surface detail as described by the KA method.

Eqs. (9) and (11) are directly expressed in Fourier space as:

$$G^{KA}(r_s, r_p) = \int_{-\infty}^{+\infty} [1 + R_{ND}(K)]\tilde{g}(K, \overline{Z})\exp[iK \cdot \overline{R}]dK, \quad (12)$$

$$\frac{\partial G^{KA}(r_s, r_p)}{\partial \hat{n}_p} = \int_{-\infty}^{+\infty} [1 - R_{ND}(K)]\frac{\partial \tilde{g}(K, \overline{Z})}{\partial \overline{Z}}[iK \cdot \overline{R}]dK,$$

where $(\overline{R}, \overline{Z})$ are the coordinates of $|r_s - r_p|$ with respect to the plane defined by $\hat{n}(r_p)$ as shown in FIG. 3(b), $$\overline{Z} = (r_s - r_p) \cdot [-\hat{n}(r_p)],$$

$$\overline{R} = \overline{Z} - (r_s - r_p). \quad (13)$$

In Eq. (12) the Fourier transform of the 3D homogeneous Green's function $\tilde{g}$ is given by (Goodman J W, Introduction to Fourier Optics. New York: McGraw Hill 1968):

$$\tilde{g}(K, \overline{Z}) = \frac{i}{2\pi D}\frac{\exp[i\sqrt{\kappa^2 - K^2}|\overline{Z}|]}{\sqrt{\kappa^2 - K^2}}, \quad (14)$$

$$\frac{\partial \tilde{g}(K, \overline{Z})}{\partial \overline{Z}} = \frac{1}{2\pi D}\exp[i\sqrt{\kappa^2 - K^2}|\overline{Z}|].$$

where vector K is defined above for Eq. (10). (It should be noted, that a similar expression can be reached for diffusive/diffusive interfaces, by means of the corresponding reflection and transmission coefficients (Ripoll et al., *Opt. Lett.* 24:796-798, 1999)).

N-Order Diffuse Reflection Boundary Method (DRBM)

In most practical cases a more accurate solution of Eq. (8) than the one given by the KA is needed. Thus, this invention describes and teaches the use of an iterative approach that uses an arbitrary number of multiple reflections from the boundary. This approach, called the N-order Diffuse Reflection Boundary Method (DRBM), solves the exact integral Eq. (8) by iteratively decomposing each reflecting event into a sum of the series. Each term in a series is referred herein as an order of reflection. The series can be truncated when the sum meets convergence criteria defined below. Thus, the DRBM method finds the solution of the exact surface integral equation Eq. (8) by representing the solution as a sum of different orders of reflection. In this manner, one can obtain fast solutions to any degree of accuracy by adding orders of reflection. This approach takes into account the shadowing effect due to the higher reflection orders (i.e., the effect caused at those areas where the source is not directly visible due to the presence of the interface), and the high reflectivities at the interfaces (i.e., high values of the reflection coefficient Eq. (10) that introduce multiple scattering interactions at the boundary) can be modeled up to any degree of accuracy. The set of N iterations can be performed without steps of matrix inversion or solving a system of equations. Hence, the computation time of the DRBM is extremely low when compared to a rigorous numerical method such as the ET or BEM, whereas the accuracy is greatly enhanced compared to the KA.

In practice, the number of DRBM orders needed may not exceed two, due to the fact that DPDWs are highly damped (i.e., suffer from strong absorption on propagation) so that multiple scattering of DPDWs along the boundary rarely takes place. About one or two first orders of the DRBM are crucial for Eq. (8) in the case of non-convex surfaces that create shadowing. This is because the $1^{st}$ or at most $2^{nd}$ order scattering with the convex interface models for the local illumination of the shadowed region from a secondary source reflected from the interface.

To develop the DRBM method, Eq. (8) is written in an iterative manner by using the Euler method with an evolution step τ (C. Macaskill and B. J. Kachoyan, Applied Optics 32, 2839-2847, 1993), and the assumption that the detectors are located at each of the surface points:

$$G^{(N)}_{DRBM}(r_s, r_p)|_{r \in S} = G^{(N-1)}_{DRBM}(r_s, r_p)|_{r \in S} \quad \text{(DRBM. 1)}$$

$$-\tau g(\kappa|r_s - r_p|) + \tau \frac{1}{4\pi}\int_S \left[\frac{\partial g(\kappa|r' - r_p|)}{\partial n'} + \frac{1}{C_{nd}D}g(\kappa|r' - r_p|)\right]G^{(N-1)}_{DRBM}(r_s, r')dS'.$$

where $G^{(N)}_{DRBM}(r_p)$ is the N-order Green function in the DRBM approximation. Equation (DRBM.1) is the main expression for the N-order DRBM. In order to find the solution to the integral in Eq. (DRBM.1) care must be taken when approaching values $r' \to r_p$ where the Green function diverges. In this case, the Green function at $r' \to r_p$ should be replaced by so-called self-induction values.

These values are well known and are dependent on the medium and surface discretization area (Yaghjian, *Proc. of the IEEE* 2:248-263 (1980), the entire teachings of which are herein incorporated by reference). The $0^{th}$-order $G_{DRBM}$ term is calculated by solving Eq. (8) using the KA method; all subsequent orders are calculated using equation (DRBM.1) in an iterative manner. The choice of the evolution step τ will affect the speed of convergence and may be optimized. A possible optimized value of τ is τ=2imag{κ}/√W+1, where W is mean diameter of the volume. Other values of τ may also be found, for example by using matrix pre-conditioners (C. Macaskill and B. J. Kachoyan, Applied Optics 32, 2839-2847 (1993), the teachings of which are incorporated here in their entirety).

Once the expression at the boundary for the N-th approximation is obtained through Eq. (DRBM.1), the intensity $U_{DRBM}$ anywhere inside the diffusive volume can be found through:

$$G^{(N)}_{DRBM}(r_s, r_d) = g(\kappa|r_s - r_d|) + \quad \text{(DRBM. 2)}$$

$$\frac{1}{4\pi}\int_S\left[\frac{\partial g(\kappa|r' - r_d|)}{\partial n'} + \frac{1}{C_{nd}D}g(\kappa|r' - r_d|)\right]G^{(N)}_{DRBM}(r_s, r')dS'.$$

$$U^{(N)}_{DRBM}(r_d) = \int_V S(r')G^{(N)}_{DRBM}(r', r_d)dr'$$

It is worth noting that a direct relation between computing times for different orders can easily be found by:

Time{DRBM(N>2)}=(N−1)*[Time{DRBM(2)−Time{DRBM(1)}]

In the following paragraphs, preferred embodiments of the invention are described that further accelerate the computation of $U^{(N)}_{DRBM}(r_p)$ using equation (DRBM.1).

Adaptive-DRBM

In a preferred embodiment of the invention, the DRBM can adaptively adjust the number of N-order reflections. In one embodiment, the adaptive adjustment can be achieved by detecting complex boundaries, i.e., surfaces with high spatial variation, by monitoring the gradient of the boundary and automatically increasing the density of local surface discretization i.e., the number of discretization areas that define surface S at that local point, and the number of orders of reflections to include in the DRBM calculations. (It is worth noting that in the case of a plane interface, the $0^{th}$ order DRBM yields an exact solution.) As used herein the spatial variation is high if substantial spatial changes occur in a range shorter than the decay length ($L_d$) of the diffusive wave. Therefore higher numbers of discretization areas need to be included for those regions where $|\nabla S| \cdot L_d > 1$, increasing proportionally with $|\nabla S|$. The decay length depends on the optical properties of the medium and the modulation frequency (with CW illumination is in the order of a few cm in the Near-infrared for tissue) and is defined as the inverse of the imaginary component of the complex wave number κ, $L_d = 1/\text{Im}\{\kappa\}$ where $\kappa = (-\mu_a/D + i\omega/cD)^{1/2}$.

In another embodiment, the adaptive adjustment can be achieved by monitoring the relative change in value of the calculated intensity added by each iteration step and stopping the number of iterations based on a convergence criterion. Typical criteria include limits on the relative change in a value of a function after each iterated step and limits on new contributions of the new iteration step to the overall value of the intensity. For example, the iterative process can be stopped when the relative change in the value of intensity falls below about 0.1% to about 10%, preferably below 1%. In another example, the iterative process can be stopped when a new contribution falls under a certain threshold value ξ. The threshold value can be selected, for example, to be about twice the value of noise.

Additionally, since the DRBM is based on a surface integral equation (DRBM.1) for waves in an absorbing medium, not all surface points contribute equally to the intensity at a certain detector point since the distances between each surface point and the detector vary. Therefore, contribution from surface points further away from the detector will suffer higher attenuation on propagation than points nearer to the detector. Therefore, in another embodiment of the invention, a threshold value that determines which surface points and their corresponding surface values $G_{DRBM}(r_s,r)|_{r \in S}$ are taken or discarded in the surface integral equation (DRBM.1) can be selected so that only surface points that satisfy the condition:

$i_{thresh} \equiv g(r_s, r_p)|_{r_p \in S} > \text{thresh}$ $S \rightarrow S(i_{thresh})$ where $i_{tresh}$ is an index of a surface point, will be considered when modeling the total intensity at the detector. Here $S(i_{tresh})$ is the total surface considered in Eqs. (DRBM.1) and (DRBM.2), and g(r) is defined above by Eq. (4).

Increasing Time Efficiency

In another embodiment of the invention, a convenient approximation to the solution of Eq. (8) may be found by the method of images. The method of images is applied by taking into account the boundary condition at a diffusive/non-diffusive interface given by Eq (7), which can be approximated to:

$$G(r_s, r) \sim G(r_s, r[z=0]) \exp(-C_{nd} D \cdot z), z > 0 \quad (17)$$

where $C_{nd}$ and D are defined above for Eqs.(3) and (8) and z is a coordinate along the direction normal to the local tangent plane and pointing into the non-diffusive medium (U or G is defined at the interface, i.e., U approached from inside or from outside must be equivalent and z must be non-negative). For convenience a planar interface is assumed at z=0 in Eq. (17). Using Eq. (17), the boundary condition (7) can be approximated to one that makes the diffuse intensity U equal to zero at a fictitious boundary at $z_{ext} = C_{nd} D$ such that $$G(r_s, r[z=C_{nd}D])=0.$$

In this way, the boundary values for the $0^{th}$ order DRBM can be found as:

$$G_{DRBM}^{(0)}(r_s, r_p) = [g(\overline{R}, \overline{Z}) - g(\overline{R}, \overline{Z} + C_{nd}D)]. \quad (\text{DRBM.3})$$

where $r_p$ is a point at the surface S and g is the infinite homogenous Green function defined by Eq. (4), $(\overline{R}, \overline{z})$ are defined above by Eq. (13), $C_{nd}$ and D are defined above for Eqs. (3) and (8), and their product represents a fictitious distance $z_{ext}$ from the real boundary at which the intensity is approximately zero.

With this expression, the $1^{st}$ order DRBM can be calculated assuming a source at $r_s$, and a detector at $r_d$, both inside the diffusive volume, as a summation over N locally planar discrete areas ΔS as:

$$G_{DRBM}^{(1)}(r_s, r_d) = g(r_s - r_d) - \frac{1}{4\pi} \sum_{p=1}^{N} \left[ \frac{\partial g(\kappa|r_p - r_d|)}{\partial n_p} + \frac{1}{C_{nd}D} g(\kappa|r_p - r_d|) \right] \Delta S(r_p) \times \times [g(\overline{R}, \overline{Z}) - g(\overline{R}, \overline{Z} + C_{nd}D)] \quad (\text{DRBM. 4})$$

Here the infinite space Green function g is defined above, $\Delta S(r_p)$ is defined as the discretized surface area at point $r_p$, $C_{nd}$ and D are defined above for Eqs. (3) and (8) and R and Z are defined above for Eq. (13). Using this new expression, computation times are greatly diminished, since it is an analytical approach and may not involve any Fourier transforms.

Application to Non-Contact Measurements

The method of the instant invention can be applied both to contact and non-contact measurements, as well as for any diffuse and non-diffuse interfaces as related to forming a tomographic image using waves and including. As used herein, the term "contact measurement" means measurement that takes place with the detector in contact with the surface or at a distance of less than about 1 mm from the surface. The term "non-contact measurement" refers to measurements that take place with the detector at a distance of greater than 1 mm from the surface. The contemplated waves include light waves, infra-red waves, waves of temperature, acoustic waves and the like. Contemplated modes of tomography include optical tomography, fluorescence-mediated tomography, near-field optical tomography, tomography with temperature waves and generally any surface-bounded inversion problems of tissues and other diffuse or diffuse-like or highly scattering medium.

Figure 11:
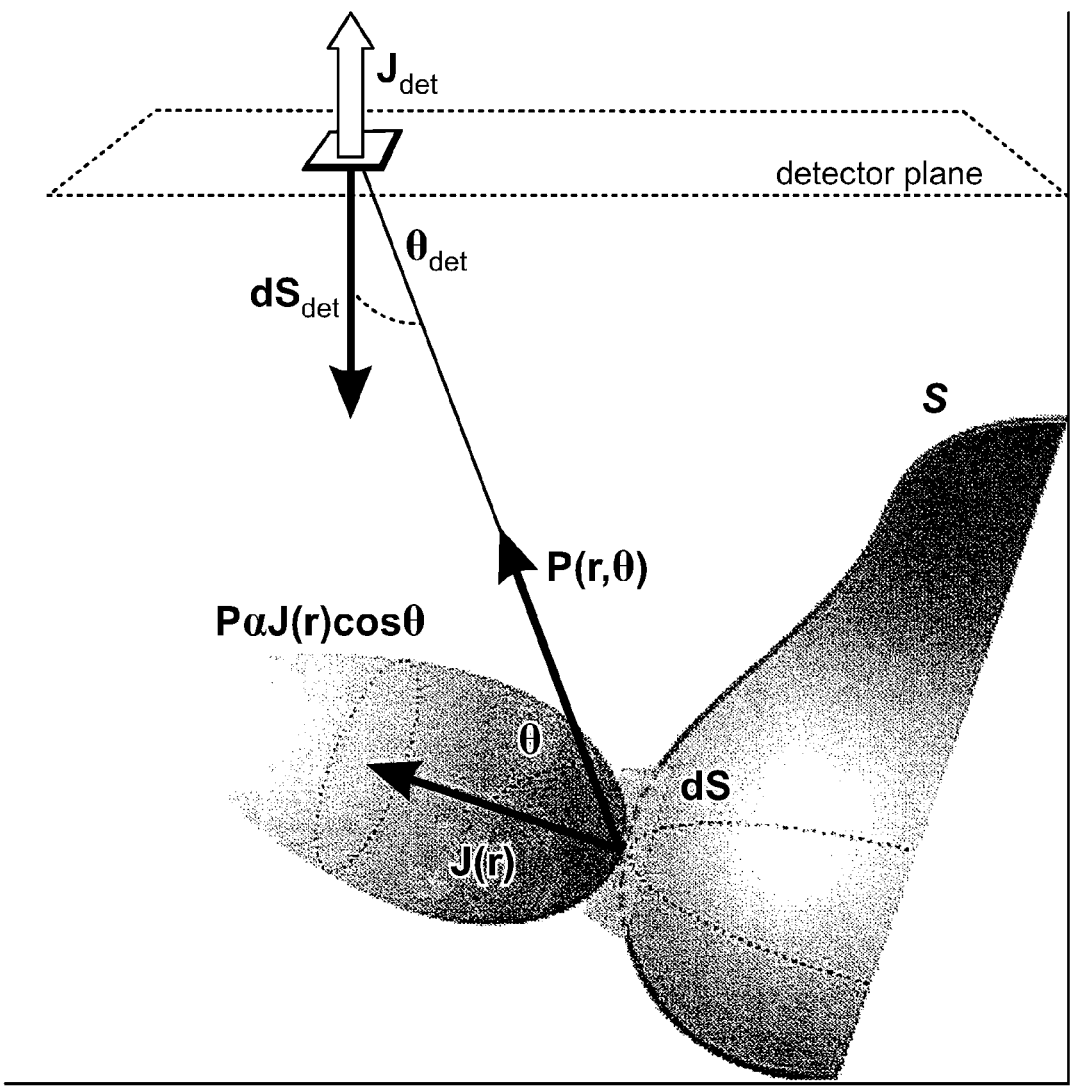
FIG. 11 is a schematic of a geometrical scheme assumed for non-contact measurements from diffusive medium.

The application of DRBM to performing non-contact measurements will now be described. Referring to the geometrical scheme described in FIG. 11 and by using Eq. (20) below, the flux $J_n$ at any point of the boundary between the diffusive and non-diffusive medium can be found as:

$$J_n(r_p) = -D\frac{\partial U(r_p)}{\partial \hat{n}_p} = \frac{1}{C_{nd}} U(r_p) \quad (20)$$

where $U(r_p)$ is defined as the average intensity at the surface point $r_p$, $C_{nd}$ and D are defined above for Eqs. (3) and (8), $r_p$ is a point on the boundary, $n_p$ is a unity vector normal to the boundary at point $r_p$ and directed towards the non-diffusive medium. As used herein, the term flux is defined as the power flowing through a surface S within an interval of time t and has units of power per area per second in the time-domain and units of power per area in the frequency or CW domain. The flux detected at any point r in the non-scattering (i.e., non-diffusive) medium, can be represented as:

$$J(r) = \frac{1}{\pi}\int_S J_n(r_p)\Gamma(r_p - r)\,dr_p \quad (21)$$

where $\Gamma(r_p-r)$ is a function defined in Eq. (22), which maps surface values $r_p$ at S onto a non-contact detector at r, and the integration is performed over all the surface points.

The expression for $\Gamma$ in Eq. (21) is given by:

$$\Gamma(r_p - r) = \frac{\exp\left(i\frac{\omega}{c}|r_p - r|\right)}{|r_p - r|^2}\xi(r_p - r)\cos\theta_p\cos\theta,$$

$$\cos\theta_p = n_p \cdot \frac{(r - r_p)}{|r - r_p|},$$

$$\cos\theta = n \cdot \frac{(r_p - r)}{|r_p - r|}, \quad (22)$$

where $\omega$ is the light wave frequency, c is the speed of light, $r_p$ and r are defined above for Eqs. (20) and (21), $\xi$ is the visibility factor, which is either unity, if both points $r_p$ and r can be joined by a straight line without intersecting the surface interface, i.e., when they are visible to each other, or zero otherwise. In Eq. (22), n is a unity vector normal to the surface of the detector or detector plane at point r of the non-scattering medium where the flux J is measured. The numerical aperture (NA) of the detector, may be represented by a general function f which models light detection at different angles at the detector position r. Including function f, Eq. (22) can be rewritten as:

$$\Gamma(r_p - r) = f(NA, \sin\theta)\frac{\exp\left(i\frac{\omega}{c}|r_p - r|\right)}{|r_p - r|^2}\xi(r_p - r)\cos\theta_p\cos\theta,$$

$$\cos\theta_p = n_p \cdot \frac{(r - r_p)}{|r - r_p|},$$

$$\cos\theta = n \cdot \frac{(r_p - r)}{|r_p - r|}, \quad (23)$$

An example of a function f which represents the NA of the detector would be a Gaussian function with full width at half-maximum equivalent to the NA:

$$f = \exp(-\sin\theta^2/NA^2).$$

Upon discretization of surfaces called for by the DRBM, Eq. (21) can be rewritten as:

$$J^{DRBM}(r) = \frac{1}{\pi}\sum_p J_p^{DRBM}(r_p)\Gamma(r_p - r)\Delta S(r_p) \quad (24)$$

In order to find the average intensity U at the detector, we will approximate it by $U(r) = C_{nd}J(r)$, where now $C_{nd}$ is defined for the detector/non-diffusive medium interface according to Eq. (8).

The expression Eq. (24) for non-contact detectors is independent of the sources. In order to obtain an expression for non-contact sources, the same formulation can be used, due to the source-detector invariance.

It is to be understood that while the invention has been described in conjunction with the detailed description thereof, the foregoing description is intended to illustrate and not limit the scope of the invention, which is defined by the scope of the appended claims.

Preferred Embodiments of the Invention

In a preferred embodiment, the present invention is a method for tomographic imaging of medium comprising directing waves into a medium having a boundary S; detecting an intensity of waves emitted from the medium by using contact or non-contact measurements of waves outside the medium; and processing the detected intensity to generate a tomographic image. The medium is diffusive or non-diffusive. Preferably, the medium is a diffusive medium. In one preferred embodiment, the medium fills an object of volume V, at least partially bounded by the boundary surface S.

The waves are directed into the medium by a source. The waves directed into the medium to be imaged can be waves of temperature, waves of light or acoustic waves. Light is preferred. Near-infrared light is most preferred.

The light source of the imaging system of the instant invention can be one or more sources specific to different chromophores, fluorophores or fluorescent imaging probes. Laser diodes can be used as light sources since they produce adequate power, are within the FDA class I and class II limits, and are stable, wavelength-specific and economical. Alternatively, filtered light can also be used.

The processing step includes representing the contribution of each wave into the detected intensity as a sum of an arbitrary integer number N of terms in a series. Each term in the series is an intensity of a wave reflected from an arbitrary surface within or outside the medium. In a preferred embodiment, the processing step includes solving the equation (DRBM.1) for an unknown function $G_{DRBM}^{(N)}$, where $G^{(N)}_{DRBM}(r_p)$ is the N-order Green function in the DRBM approximation, $C_{nd}$ is as previously defined in Eq. (8), D is the diffusion coefficient inside the diffusive medium, n is a unity vector normal to boundary surface S and pointing into the non-diffusive medium, $\kappa$ is a diffusive wave number $\kappa = \sqrt{-\mu_a/D + i\omega/c}$, for a modulation frequency $\omega$, c is a speed of light in the medium, $\mu_a$ is an absorption coefficient, $\tau$ is an evolution step, and $r_s$, and $r_p$ are source and detector positions respectively, and wherein the detector is located at the surface, and where g is the Green's function for an infinite homogeneous diffusive medium with a wave number $\kappa$, given by formula g(κ|r−r'|)=exp [iκ|r−r'|]/D|r−r'|, and N is an arbitrary integer not smaller than 1.

In another preferred embodiment, the processing step includes solving the equation (DRBM.2) for an unknown function $G_{DRBM}^{(N)}$, where $G^{(N)}_{DRBM}(r_p)$ is the N-order Green function in the DRBM approximation, $C_{nd}$ is as previously defined in Eq. (8), D is the diffusion coefficient inside the diffusive medium, n is a unity vector normal to boundary surface S and pointing into the non-diffusive medium, κ is a diffusive wave number $κ=\sqrt{-μ_a/D+iω/c}$, for a modulation frequency ω, c is a speed of light in the medium, $μ_a$ is an absorption coefficient, τ is an evolution step, and $r_s$, and $r_p$ are source and detector positions respectively, and wherein the detector is located at the surface, and where g is the Green's function for an infinite homogeneous diffusive medium with a wave number κ. Given by formula g(κ|r−r'|)= exp [iκ|r−r'|]/D|r−r'|, N is an arbitrary integer not smaller than 1, $U_{DRBM}^{(N)}(r_d)$ is a wave intensity at point $r_d$, and S(r') is the strength of the light source at position r' expressed in units of energy density.

The processing step can further include monitoring a gradient of the boundary surface to detect complex boundaries and automatically increasing a density of local surface discretization and the number N of terms in a series, if the boundary is complex. Alternatively, the processing step includes monitoring relative change in a value of the calculated intensity added by each term of the series and truncating the series by selecting a finite number N of terms in a series, when the relative change in a value of the calculated intensity meets convergence criteria. In a preferred embodiment, the processing step comprises monitoring the gradient of a surface boundary to detect complex boundaries, automatically increasing a density of local surface discretization and the number N of terms in a series, if the boundary is complex, and optimizing an evolution step τ by assigning a value, of about $τ=2\text{imag}\{κ\}/\sqrt{W}+1$, wherein W is a mean diameter of the diffusive medium.

Preferably, the medium being imaged is filling a volume V of arbitrary geometry. Alternatively, the volume or object has a fixed geometry whose surface is defined in terms of a continuous function f[z(x,y)] in cartesian, polar or cylindrical coordinates. Arbitrary geometry is preferred. The object can be a sample of a biological tissue or an animal, including a human. The object may also be non-mammalian, i.e., *C. elegans, drosophila*, etc.

Three different source-detection technologies exist. Any combination of them can be used for tomography applications as described herein. The simplest is continuous wave (CW) imaging. This technique uses light of constant intensity and measures either (1) the signal due to a distribution of excited fluorophores or (2) the attenuation of light (due to tissue absorption and scattering) employing multiple source-detector pairs. The technique is technically relatively simple and usually offers the best signal-to-noise (SNR) characteristics. However, it is not best suited for imaging of intrinsic tissue contrast since it usually introduces significant cross-talk between the calculations and imaging of absorption and scattering coefficients. On the other hand, if the background optical properties are known, the method is well-suited for imaging fluorophore concentration in the steady-state. A more elaborate approach is to use intensity modulated (IM) light at a single or at multiple frequencies. With this method, modulated light attenuation and phase shifts, relative to the incident light, can be measured for multiple source-detector pairs. Compared to a CW measurement, which yields intensity attenuation, the IM technique offers two pieces of information, i.e., intensity attenuation and phase shift per source-detector pair. Amplitude and phase are usually uncorrelated measurements and can more efficiently resolve the absorption and scattering coefficient of intrinsic contrast. In the fluorescence mode, the technique can image two sets of information, fluorophore concentration and fluorescence lifetime. The third approach, the time-resolved (TR) technique uses short pulses of light injected into the tissue. The technique resolves the distribution of times that the detected photons travel into the medium for multiple source-detector pairs. Time-resolved methods contain the highest information content per source-detector pair, comparable only to the IM method performed simultaneously at multiple frequencies. This can be easily explained when one considers that the Fourier transform of the time-resolved data yields information at multiple frequencies up to 1 GHz, including the continuous wave components (f=0 MHz) used by the previous two methods. Therefore, the time-resolved method offers a CW component for direct comparison with the CW system, but also intensity attenuation and phase-shift measurements at multiple-frequencies (via the Fourier transform) that can image intrinsic absorption and scattering, and also fluorophore concentration and fluorescence lifetime.

The step of detection can be accomplished by either contact or non-contact measurements of emitted wave intensity. In one embodiment, contact measurements are made using optical guides, fiber guides, optical matching fluids, lenses or any combination thereof. In another embodiment non-contact measurements are made using a system of lenses, pinholes, apertures or any combination thereof. Non-contact measurements are preferred.

The method of the present invention can further include selecting a tomographic imaging method. The tomographic imaging method can be selected from the group consisting of diffuse optical tomography, fluorescence-mediated tomography, near-field optical tomography and thermal tomography.

The preferred intrinsic absorbers, fluorochrome, or scatterer is selected from the group comprising hemoglobin, water, lipid, myoglobin, tissue chromophores and organelles.

These steps can also be repeated at predetermined intervals thereby allowing for the evaluation of emitted light in an object over time.

Preferred fluorescent imaging probes that can be used with the present invention include, but are not limited to (1) probes that become activated after target interaction (Weissleder, et al., *Nature Biotech*, 17:375-378, 1999; Bremer, et al., *Nature Med.*, 7:743-748, 2001), (2) wavelength shifting beacons (Tyagi et al., *Nat. Biotechnol.*, 18:1191-1196, 2000), (3) multicolor fluorescence probes (Tyagi et al., *Nat. Biotechnol.*, 16:49-53, 1998), or (4) probes that have high binding affinity to targets, i.e., that remain within a target region while nonspecific probes are cleared from the body (Achilefu et al., *Invest. Radiol.*, 35:479-485, 2000; Becker, et al., *Nature Biotech* 19:327-331, 2001; Bujai et al., *J. Biomed. Opt.* 6:122-133, 2001; Ballou et al., *Biotechnol. Prog.* 13:649-658, 1997; Neri et al., *Nature Biotech* 15:1271-1275, 1997.), (5) or probes that by themselves that preferentially accumulate in diseased tissue at a different rate compared to normal tissue (Reynolds, et al., *Photochem Photobiol* 70:87-94, 1999; Becker et al., *Phtochem Photobiol* 72:234-241, 2000).

The methods of the invention can be used to determine a number of indicia, including tracking the localization of the fluorescent imaging probe in an object over time or assessing changes or alterations in the metabolism and/or excretion of the fluorescent imaging probe in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The invention can be used to help a physician or surgeon to identify and characterize areas of disease, such as arthritis, cancers and specifically colon polyps, or vulnerable plaque, to distinguish diseased and normal tissue, such as detecting tumor margins that are difficult to detect using an ordinary operating microscope, e.g., in brain surgery, help dictate a therapeutic or surgical intervention, e.g., by determining whether a lesion is cancerous and should be removed or non-cancerous and left alone, or in surgically staging a disease, e.g., intraoperative lymph node staging.

The methods of the invention can also be used in the detection, characterization and/or determination of the localization of a disease, especially early disease, the severity of a disease or a disease-associated condition, the staging of a disease, and monitoring and guiding various therapeutic interventions, such as surgical procedures, and monitoring drug therapy, including cell based therapies. Examples of such disease or disease conditions include inflammation (e.g., inflammation caused by arthritis, for example, rheumatoid arthritis), all types of cancer (e.g., detection, assessing treatment efficacy, prognosis, characterization), cardiovascular disease (e.g., atherosclerosis and inflammatory conditions of blood vessels, ischemia, stroke, thrombosis), dermatologic disease (e.g., Kaposi's Sarcoma, psoriasis), ophthalmic disease (e.g., macular degeneration, diabetic retinopathy), infectious disease (e.g., bacterial, viral, fungal and parasitic infections), immunologic disease (e.g., Acquired Immunodeficiency Syndrome, lymphoma, multiple sclerosis, rheumatoid arthritis, diabetes mellitus), central nervous system disease (e.g., Parkinson's disease, Alzheimer's disease), and bone-related disease (e.g., osteoporosis, primary and metastatic bone tumors, osteoarthritis). The methods of the invention can therefore be used, for example, to determine the presence of tumor cells and localization of tumor cells, the presence and localization of inflammation, including the presence of activated macrophages, for instance in athlerosclerosis or arthritis, the presence and localization of vascular disease including areas at risk for acute occlusion (i.e., vulnerable plaques) in coronary and peripheral arteries, regions of expanding aneurysms, unstable plaque in carotid arteries, and ischemic areas. The methods and compositions of the invention can also be used in identification and evaluation of apoptosis, necrosis, hypoxia and angiogenesis.

Importantly, the methods of the present invention may be used in combination with other imaging compositions and methods. For example, the methods of the present invention may be used in combination with other traditional imaging modalities such as X-ray, CT, PET, SPECT, and MRI. For instance, the methods of the present invention may be used in combination with CT and MRI to obtain both anatomical and molecular information simultaneously, for instance by co-registration of a tomographic image with an image generated by another imaging modality. In particular, the combination with MRI or CT is preferable given the high spatial resolution of these imaging techniques. DOT imaging (absorption only) has already been combined with MRI imaging (Ntziachristos et al., *Proc. Natl. Acad. Sci., USA*, 97:2767-72, 1999) while one of the examples in this application teaches how to combine FMT imaging with MRI.

EXEMPLIFICATION

The invention is further described in the following examples, which do not limit the scope of the invention described in the claims.

Example 1

Figure 4:
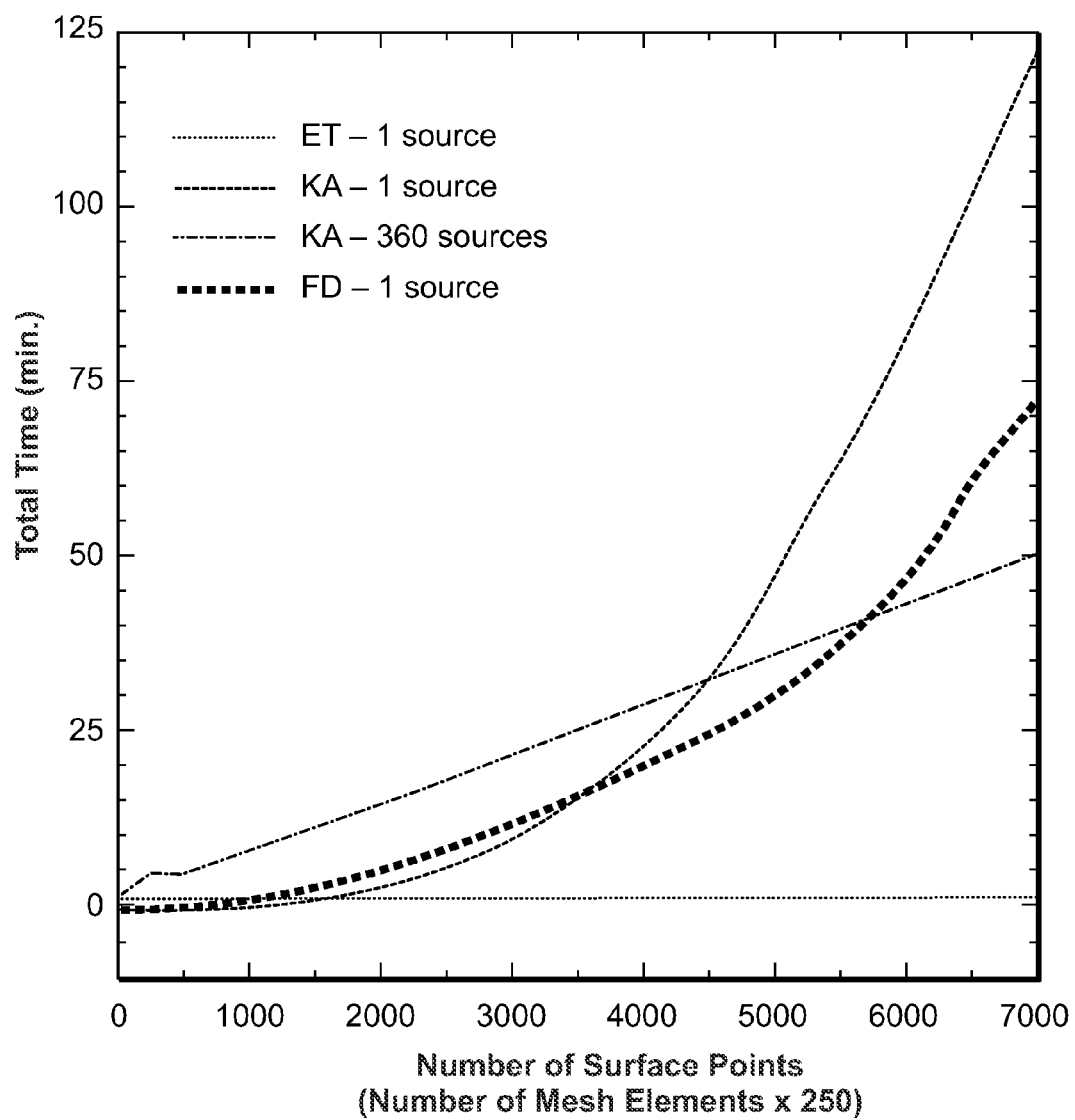
FIG. 4 is a plot of computation time of the KA method versus an exact solution using more rigorous methods.

KA is Several Orders of Magnitude Faster Than More Rigorous Numerical Methods Such as FD or ET Referring to FIG. 4, the computing times achieved by using the KA as defined by equation (12) is compared to the extinction theorem (ET) and finite-differences solution (FD). While both ET and FD methods have a strong non-linear dependence as the area of the surface and the volume investigated increases, the KA method scales linearly with the size of the problem and more importantly it is faster than the ET and FD methods by almost three-orders of magnitude.

By way of a practical example, the number of discretization points for a sphere of radius 2 cm needed in order to maintain a one transport mean free path (ltr=D/3) distance between points (N~5000) was used to compare the speed of the KA and ET methods. In this case, it takes the KA methods 70 seconds and the ET method 50 minutes to solve the problem, indicating that the KA as approximately 40 times faster than the ET method. A more realistic surface such as the adult head, would imply an equivalent radius of at least 4 cm, and thus N~20000. In this case, the KA takes on the order of 90 seconds, whereas the ET takes on the order of 45 hours for only one forward solution. In this more realistic case, the KA is 1800 times faster. Similar conclusions can be reached for the FD method. Also, due to its linearity, large numbers of surface points are possible with the KA, namely N~10E+6, whereas with the ET, such large matrices are impossible to solve at the present time.

These results indicate that utilizing KA allows fast, real-time application of optical tomographic techniques.

Example 2

The Errors of the KA Due to Shadowing Effect

So-called shadowing effect appears when certain surface areas are blocked from the source by the geometry of the interface. Since the KA only considers first order reflections at the interface, errors appear in the proximities of the shadow regions of a source. Furthermore, since these shadow areas are not taken into account in the KA, it predicts higher values of the intensity for these areas.

Referring to FIGS. 5(a)-(d), the shadow effect is demonstration of for the KA method and for the infinite case for a cylinder of R=2.5 cm with a sine profile in the boundary of amplitude 0.5 cm, and period $\pi/4$. The error is plotted as a percentage of the absolute photon field strength at each point. Error committed for different source locations using the KA are shown in (a) and (c) and using the homogeneous Green's function in (b) and (d). The following source locations were considered: ($\rho$=2.3 cm, $\theta$=0) for (a) and (b), and ($\rho$=1.5 cm, $\theta$=0) for (c) and (d). In all cases $\mu_s'$=10 cm$^{-1}$, $\mu_a$=0.1 cm$^{-1}$.

Figure 5A:
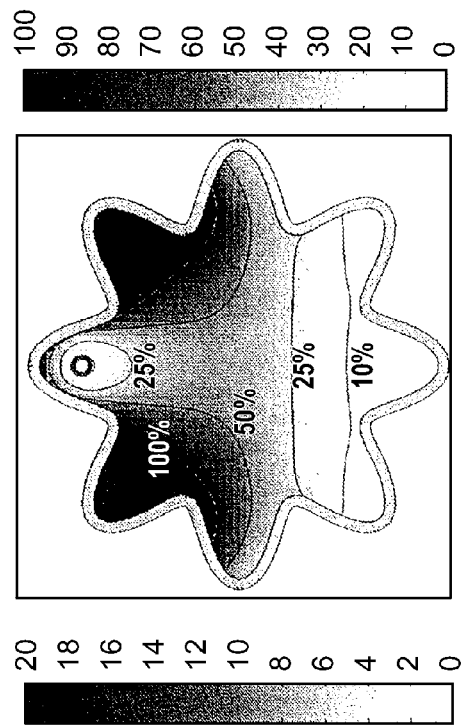
FIG. 5(a)-(d) demonstrates the shadow effect for the KA method and for the infinite case for a cylinder.
Figure 5B:
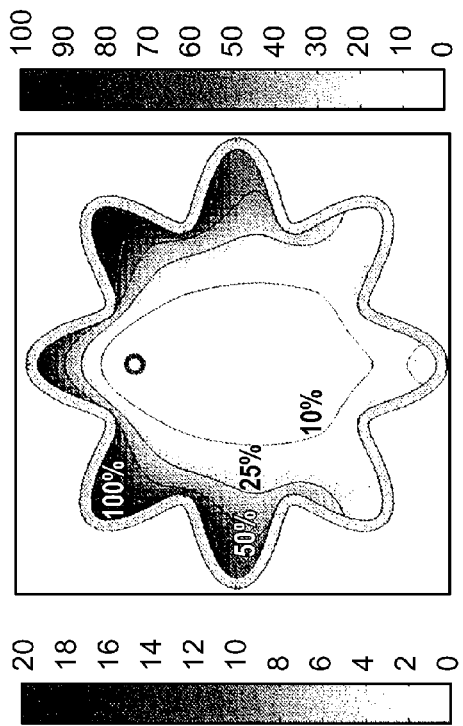
Figure 5C:
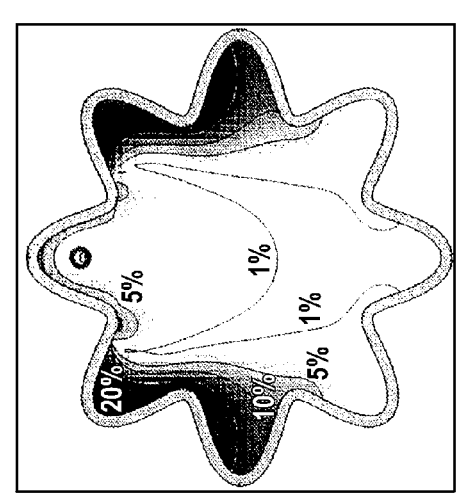
Figure 5D:
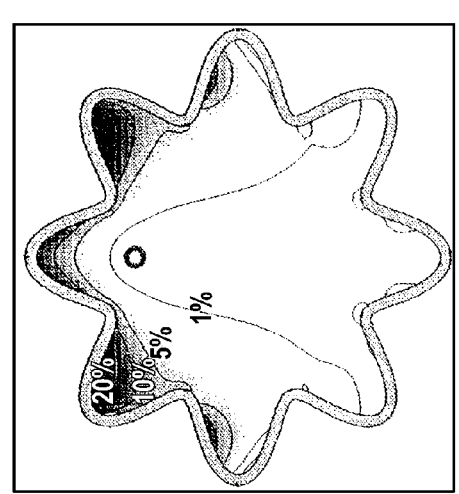

In general, it had been demonstrated that the KA calculates the average intensity with errors that are less than 5% inside the volume (see FIGS. 5(a) and (c)), but in the shadow regions near the interface, errors approach 20% or more. The errors in these regions are especially significant since they are at the boundary interfaces where the light sources and detectors would be likely located.

Example 3

The Errors of the KA when Imaging Small Volumes with Weak Absorption

Figure 6B:
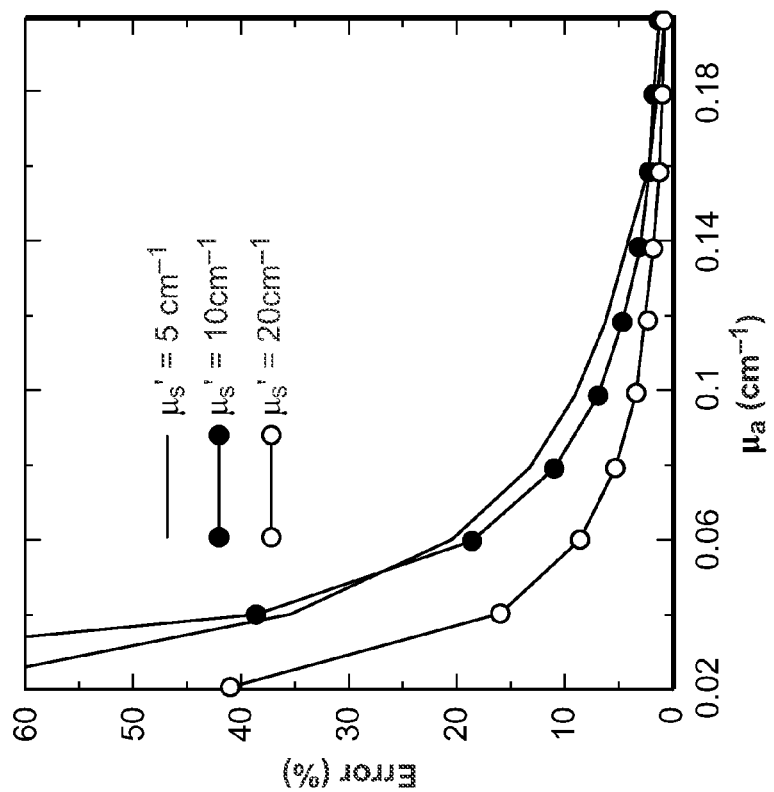
FIGS. 6(a) and (b) are plots depicting error in the KA vs. absorption coefficient for different radii and scattering coefficients for a smooth cylinder with no shadowing effect.
Figure 6A:
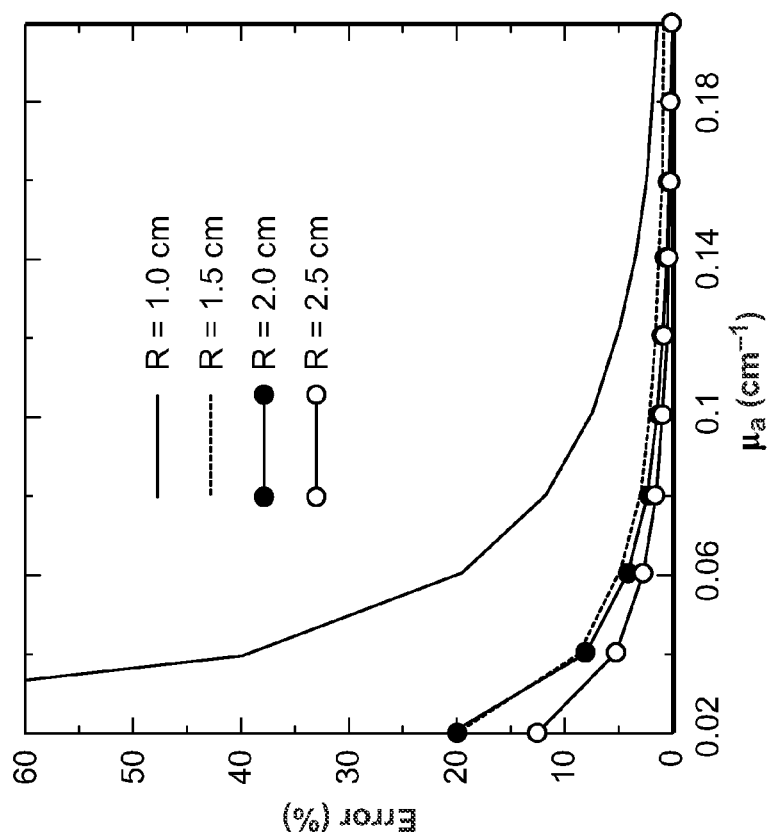

A comparison of the intensity generated by a point source in a cylindrical geometry using the KA versus the exact solution, (ET) with different several radius and optical properties is shown in FIG. 6. Error in the KA were plotted against absorption coefficient for different radii and scattering coefficients for a case of a smooth cylinder (i.e., no shadowing effect).

The smaller the dimensions of the geometry and the smaller the absorption coefficient the larger the error committed by the KA method. As seen in this figure, the error increases as the volume of the medium or the absorption decreases. From FIG. 6(a), it can be concluded that in order to make practical use of the KA (assuming a minimum of 5% accuracy), either large volumes and therefore small curvatures need to be present (R>2.5 cm), or very large absorption coefficients are needed ($\mu_a$>0.1 l/cm).

Example 4

Computation Times of the DRBM

Figure 7:
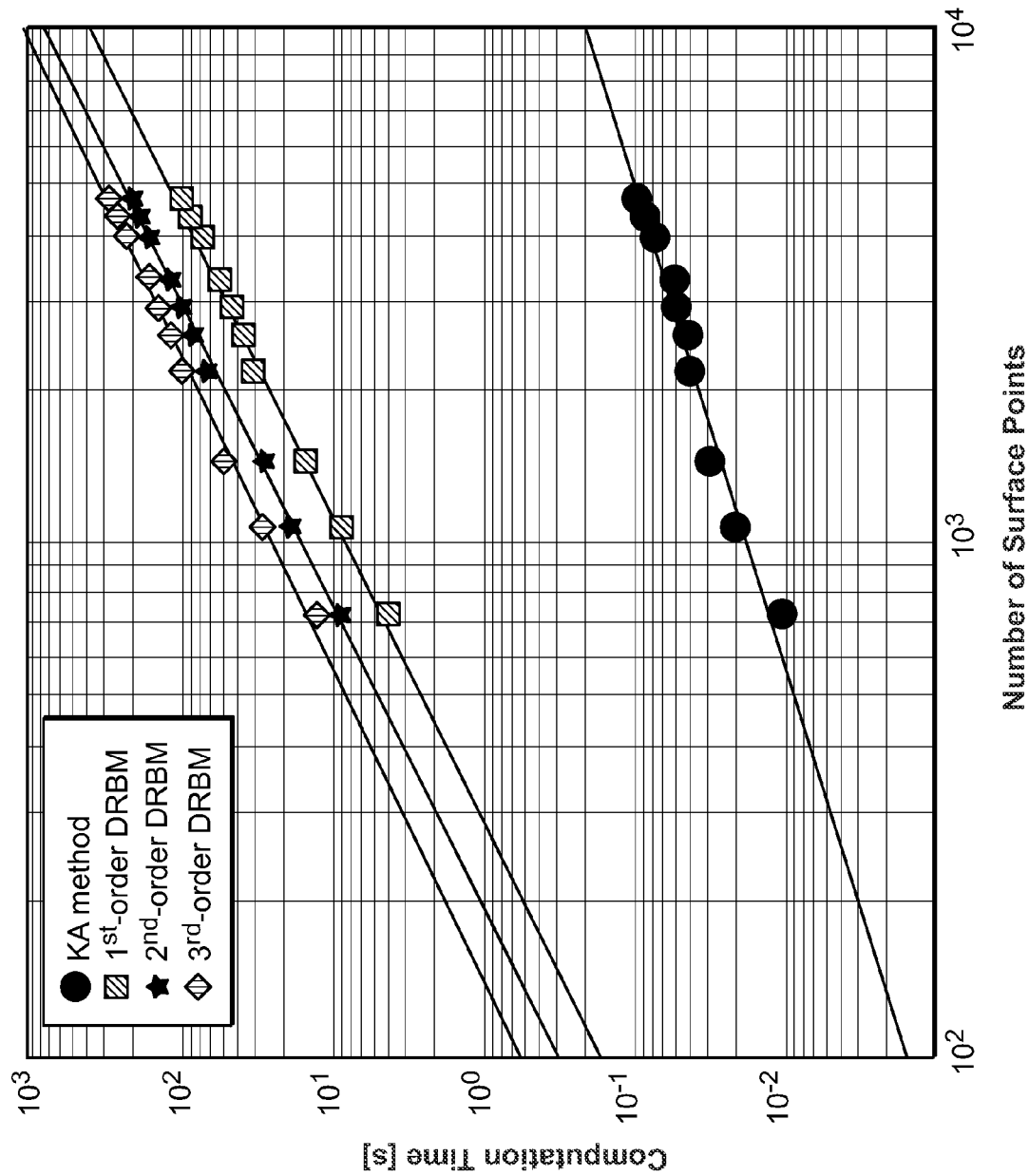
FIG. 7 is a plot showing computation times achieved with the KA and DRBM method for different N-orders.

Computation times of the first four orders of the DRBM are shown in FIG. 7. As can be seen, the computation time is still linear even when dealing with N-order approximations. While the computation time increases the linear dependence with the number of surface points remains since there is not matrix inversion involved in the DRBM method. The computations times achieved by the different orders are very close and orders of magnitude lower than numerical methods shown in FIG. 4.

Example 5

Increasing Time Efficiency

Figure 8:
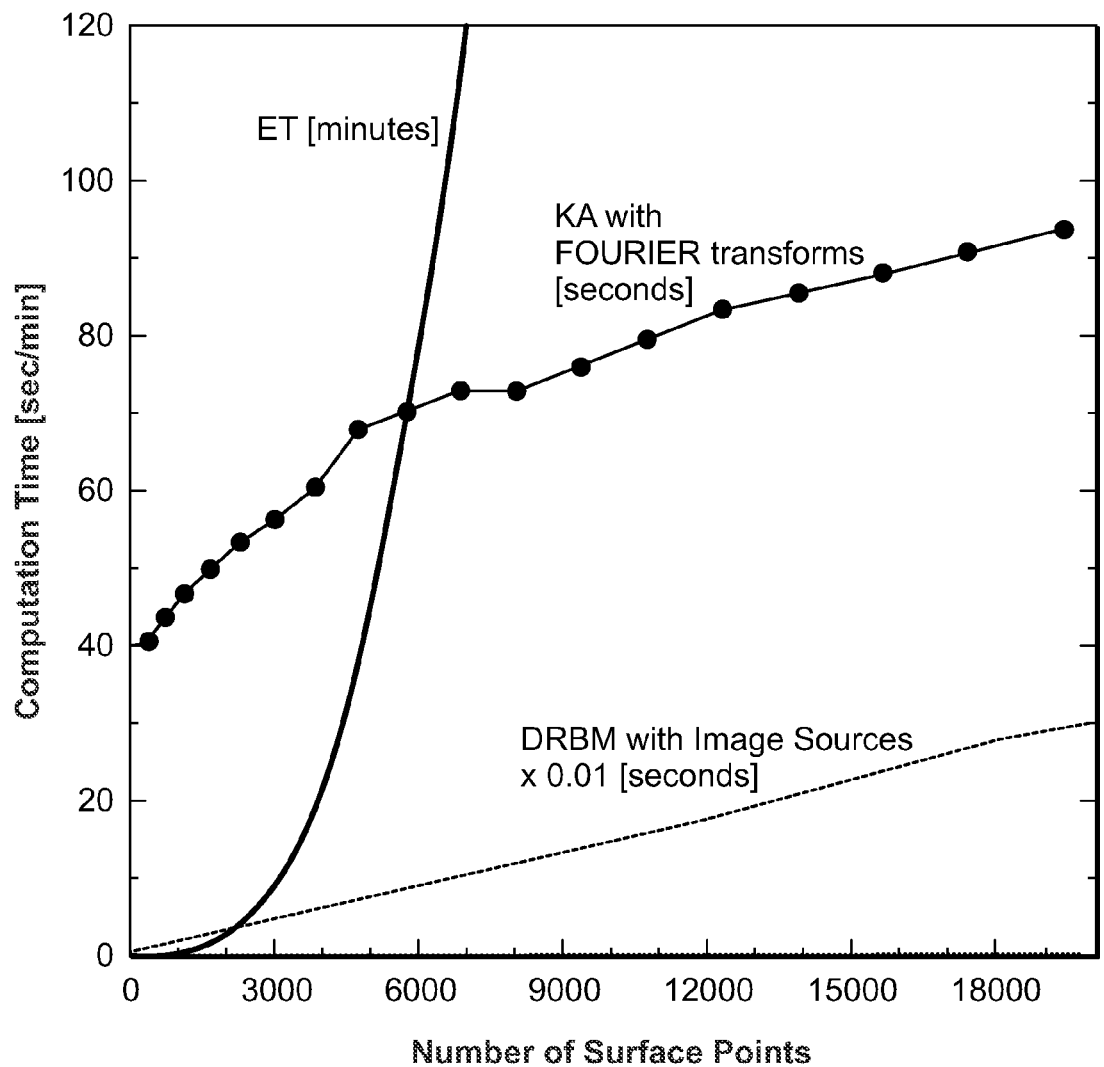
FIG. 8 is a plot showing computation time achieved with acceleration of the DRBM.

Computation times using equation (DRBM.4) for the $1^{st}$ order DRBM are shown in FIG. 8. As shown, the $1^{st}$-order DRBM with image sources is 3 orders of magnitude faster than the KA method with Fourier transforms. When compared with rigorous numerical solutions such as ET or FD, the DRBM is 5-6 orders of magnitude ($10^5$-$10^6$) faster. Higher DRBM orders impose only a slight increase in computation time as evident in FIG. 7.

Example 6

Imaging Demonstration of the DRBM

Figure 9A:
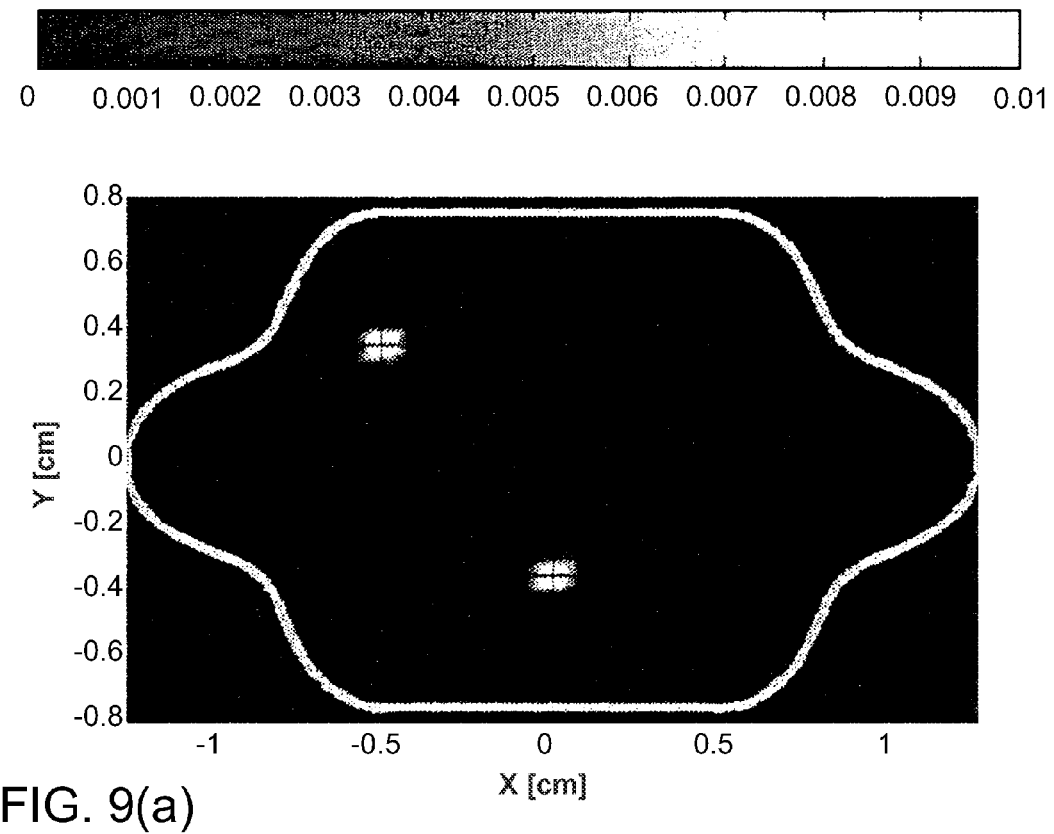
FIG. 9 depicts reconstruction of the simulated geometry in (a) using the ET method, (b) the $2^{nd}$ order DRBM for exact geometry, (c) $2^{nd}$ order DRBM for an approximate boundary indicated by the ellipsoid solid line and (d) transmittance geometry using the expression of a slab.
Figure 9B:
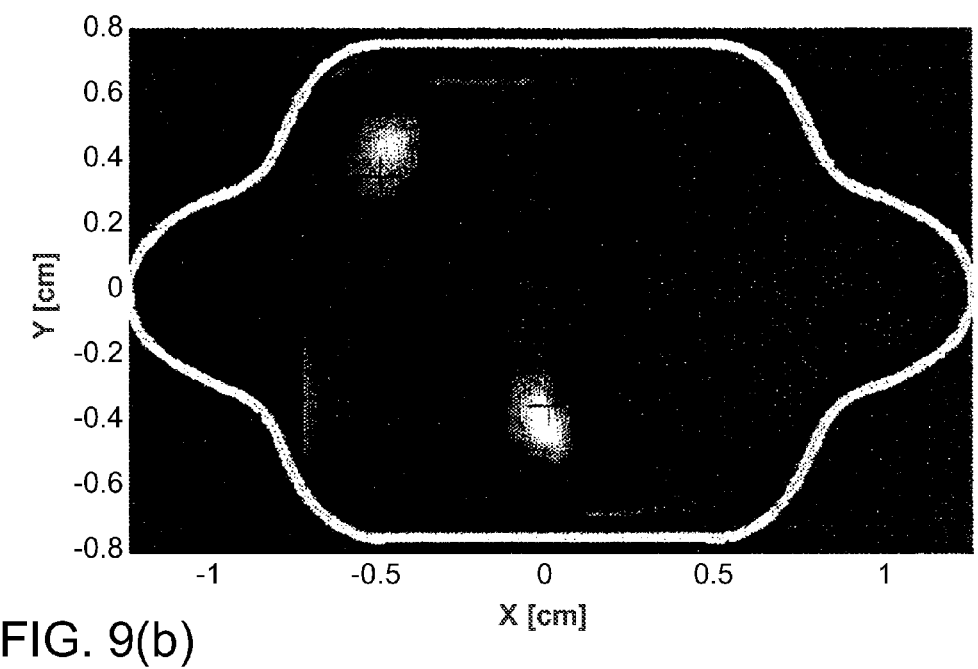
Figure 9C:
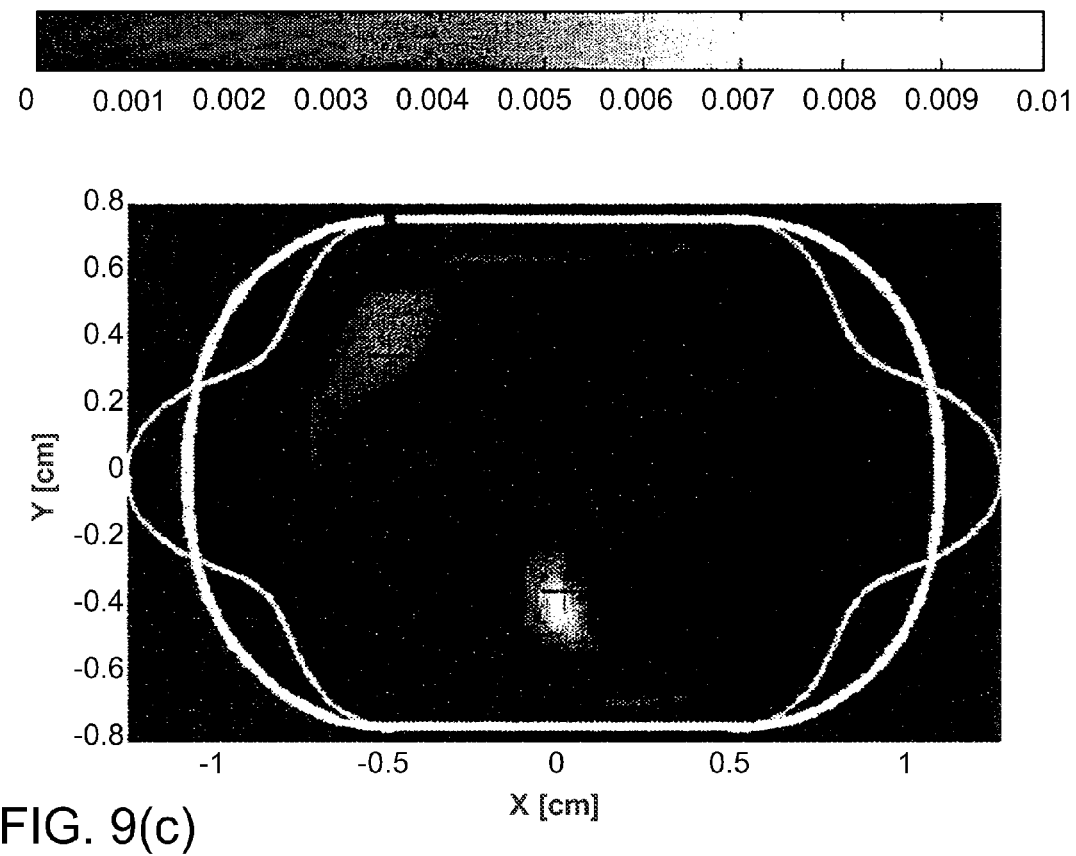
Figure 9D:
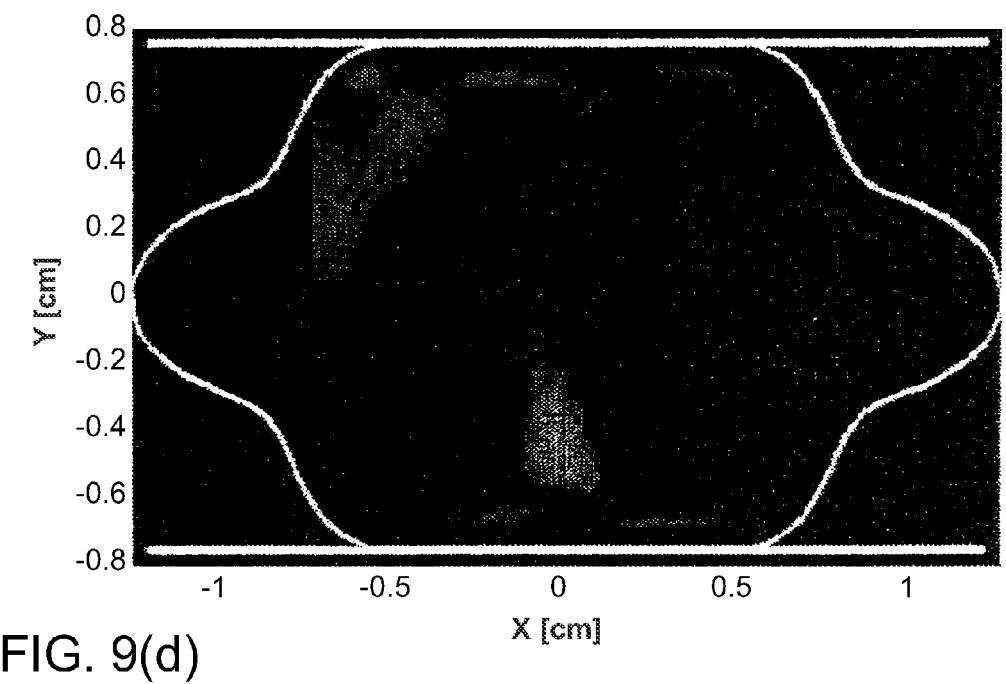
Figure 10:
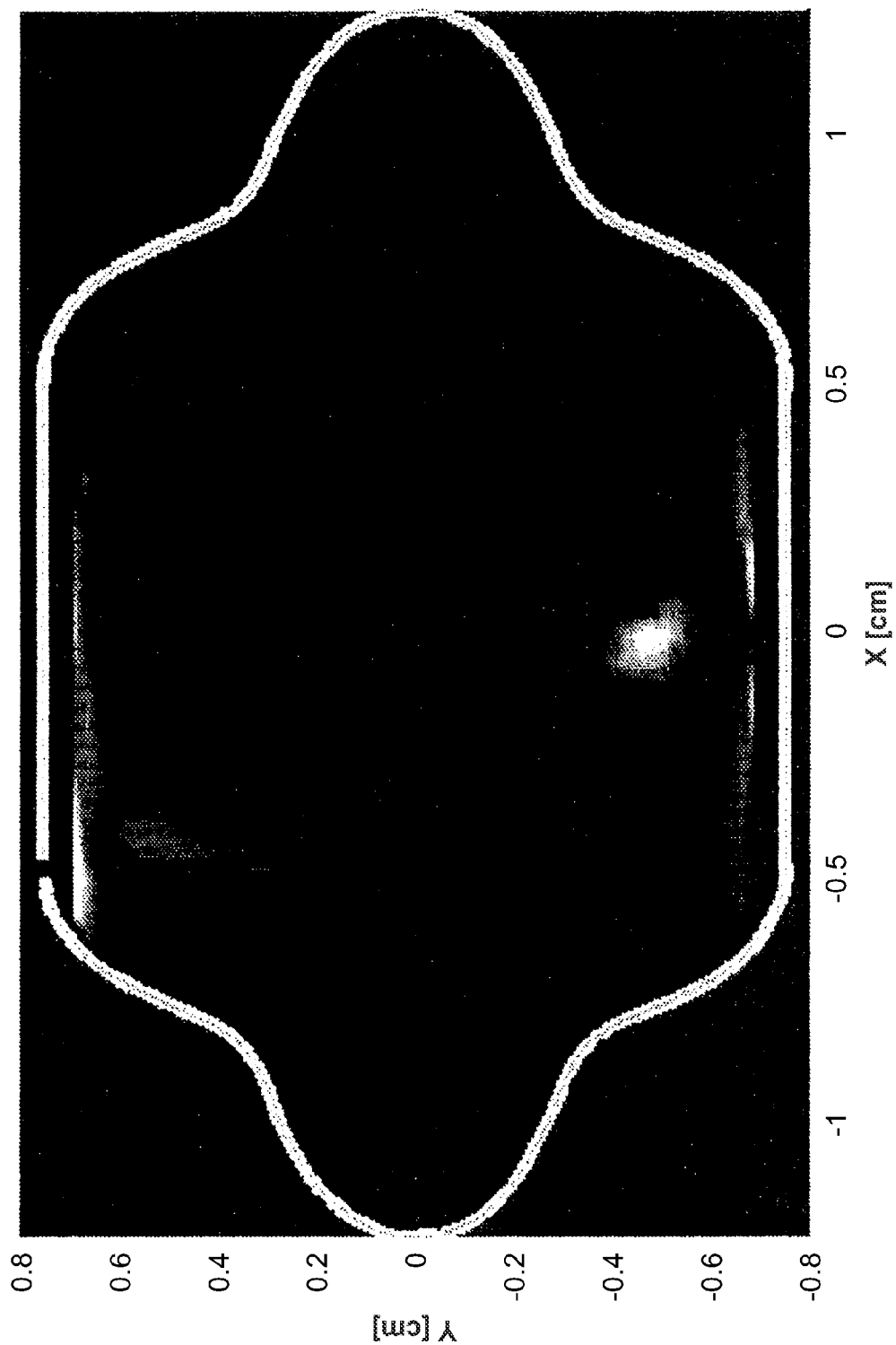
FIG. 10 depicts reconstruction of simulated geometry in FIG. 9(a) using the KA method for the exact geometry. The image demonstrates the inefficiency of the KA method to image small dimensions.

To demonstrate the efficiency of the DRBM to image small volumes with complex boundaries, simulations were performed using an exact forward solver to evaluate its performance when a) the boundary is not exactly known and b) when an approximation to the forward model is used, i.e., when one approximates the actual arbitrary boundary with a generic boundary such as an ellipse or a slab. The DRBM method was also compared to an exact solution (ET method) and to the KA method. FIG. 9 depicts reconstruction of the simulated geometry in (a) using the ET method, (b) the $2^{nd}$ order DRBM for exact geometry, (c) $2^{nd}$ order DRBM for an approximate boundary indicated by the ellipsoid solid line and (d) transmittance geometry using the expression of a slab. FIG. 9 demonstrates the effect of using geometrically accurate or geometrically approximate forward models in modeling complex boundaries and FIG. 10 depicts reconstruction of simulated geometry in FIG. 9(a) using the KA method for the exact geometry. The image demonstrates the inefficiency of the KA method to image small dimensions. In this simulation, two fluorescing objects (200 nM) are contained within a complex boundary that approximates the outline of a mouse in two dimensions. In FIG. 9(a), the forward field has been calculated analytically using an exact solution (Extinction Theorem). FIG. 9(b) depicts the reconstruction obtained using the $2^{nd}$ order DRBM. FIG. 9(c) depicts the image reconstruction using an elliptical outline also using the $2^{nd}$ order DRBM and in FIG. 9(d) shows the reconstruction obtained assuming an infinite slab with the method of image sources. It is evident that an exact knowledge of the boundary is necessary in order to obtain a high fidelity reconstruction of the underlying geometry and that our newly developed DRBM method is very efficient in doing so. For reference, FIG. 10 illustrates the results obtained when using the KA method. As can be seen from FIG. 10, the KA is not capable of reconstructing the objects accurately in this case due to the convex complex boundary and the relatively small dimensions of the problem. In fact, the results are similar to those of the slab inversion (FIG. 9(d)).

Data Collection and Processing

Figure 12A:
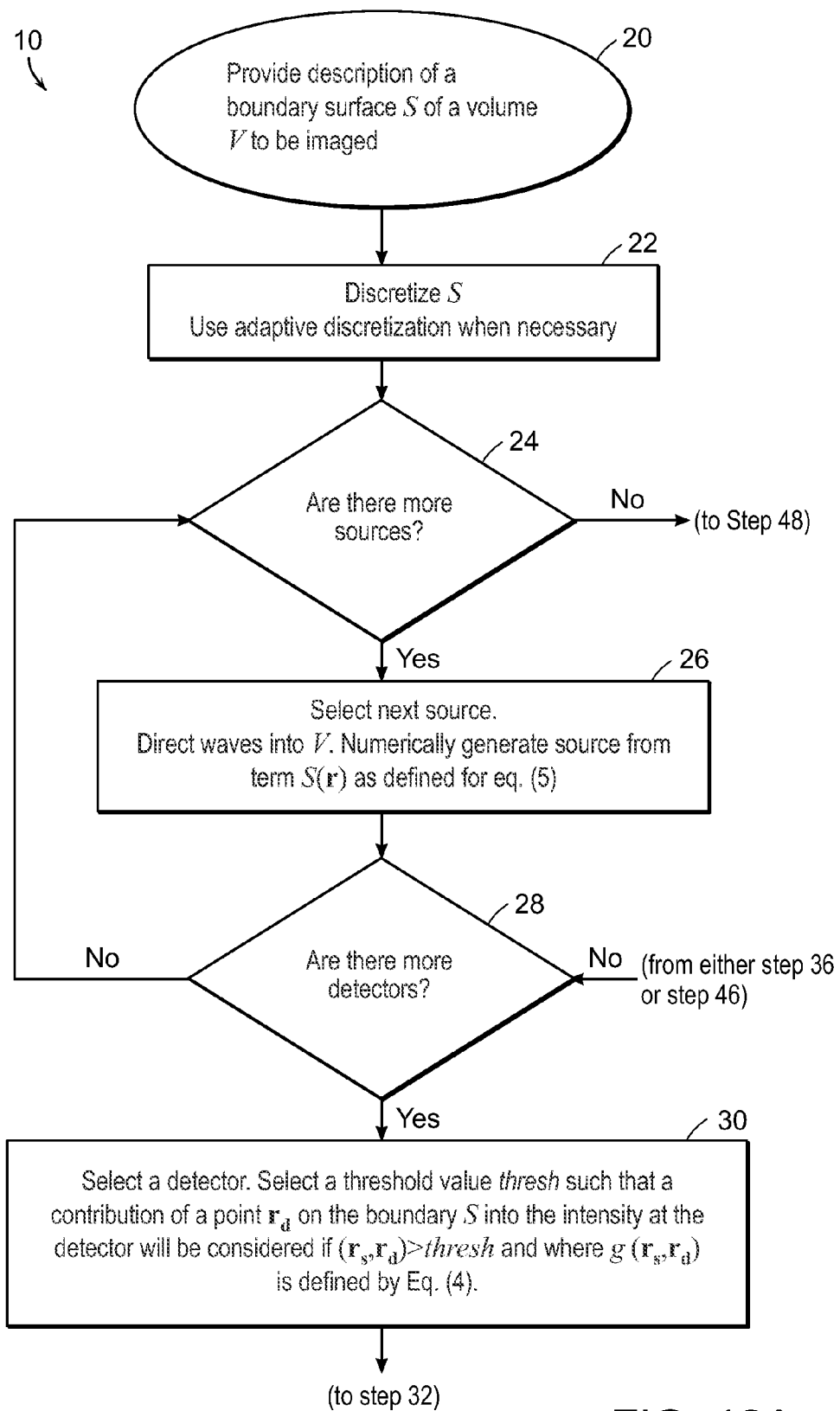
FIGS. 12A-12C is a flow diagram depicting the operation of a tomographic imaging system implementing the method of the present invention.
Figure 12B:
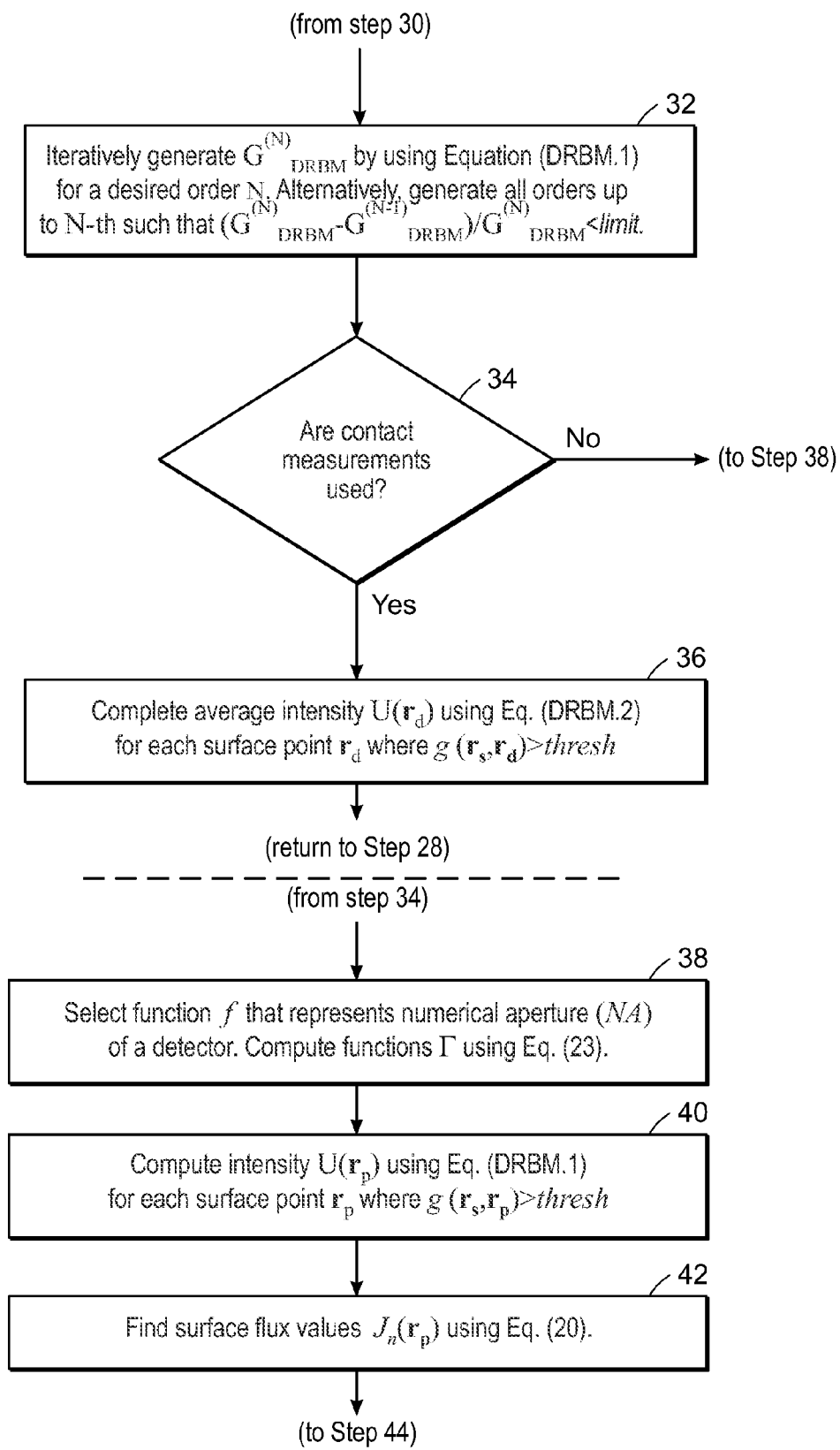
Figure 12C:
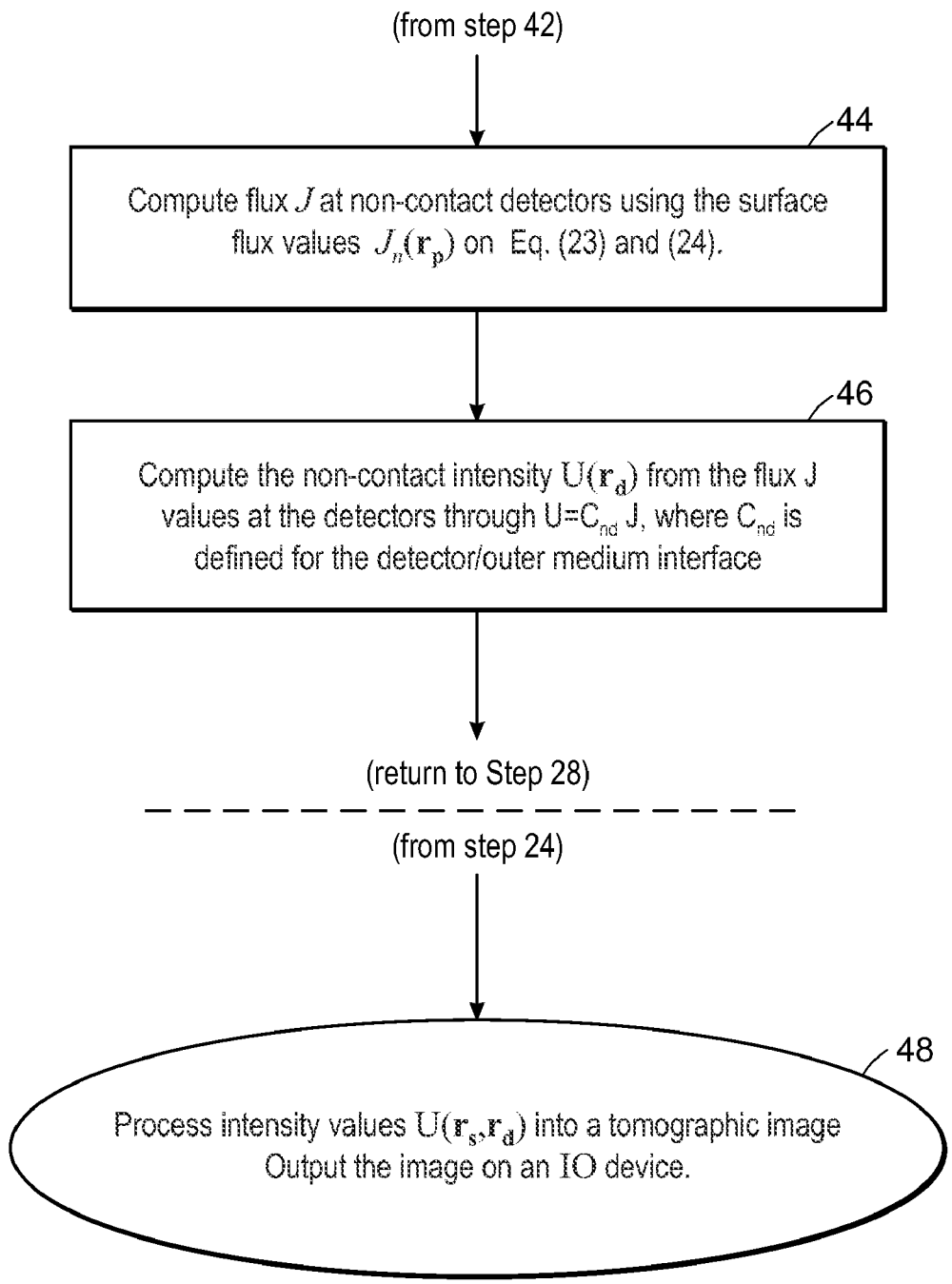

Referring to FIGS. 12A-12C, a data flow chart and a control diagram 10 is provided depicting the operation of the system and method of the present invention. Given that the waves are generated at a total of $N_{src}$ sources and detected by to a total of $N_{det}$ detectors, the method of the present invention generates data that can be processed into a tomographic image by a system of FIG. 1.

In step 20, the description of a boundary surface S of a volume V to be imaged is provided as either a collection of points or an equation. The surface S of the volume V under study that contains the target object, i.e. the object we wish to image and characterize, must be known a priori. This information may be obtained either through MRI information or any other method that gives surface information. In some cases the surface under study may be modeled through a high order polynomial of the spatial variables x and y.

In step 22, the surface S is discretized. If necessary, the number of discrete areas in those regions where the surface gradient is higher or as it is most convenient is increased to improve computation time and accuracy.

In step 24 a check is made to determine whether all sources contributed into the computed intensity. If all sources contributed, then step 48 is performed. If there are sources whose contribution was not counted, step 26 is performed.

In step 26, a source number isrc is selected and wave corresponding to the selected source are directed into the volume V. The source term distribution S(r) for source isrc is generated numerically as defined for Eq. (5). S(r) may be approximated to a point source located one transport mean free path, ltr=1/µs', where µs' is the reduced scattering coefficient within the tissue, or to a line source that decays exponentially in the direction normal to the boundary surface at the point of incidence. Alternatively, the non-contact formulation presented above by Eqs. (20)-(24) can be used to find flux and intensity at the boundary S generated by the selected source.

In step 28, a check is made to determine whether all the detectors from the total number of Ndet were used to detect the signal generated by the detector selected in step 26. If all detectors were used, control is passed back to step 24. If there are detectors that were not used to detect the selected source, step 30 is performed.

In step 30, a detector number $i_{det}$ is selected. A threshold value thresh is selected such that a contribution of a point $r_p$ on the boudary S into the intensity at the detector will be considered if $i_{thresh}=g(r_s,r_p)|_{r_p \in S}$>thresh and where $g(r_s,r_p)$ is defined by Eq. (4). The zero-th order Green function of Eq. (DRBM.3) is found at each point of boundary S that satisfies the above condition.

In step 32, Green's function $G_{DRBM}^{(N)}$ is iteratively generated using Eq.(DRBM.1) for the desired order N. Alternatively, all orders N are generated until such order that $((G_{DRBM}^{(N)}-G_{DRBM}^{(N-1)}/G_{DRBM}^{(N)})$ is less than a selected value.

In step 34, a determination is made of whether contact measurements are used. If contact measurements are used, step 36 is performed. If non-contact measurements are used, step 38 is performed.

In step 36, the average intensity $U(r_d)$ is computed using Eq.(DRBM.2) for each point $r_d$ where $g(r_s,r_d)_{r_d \in S}$>thresh. Then, the control is passed back to step 28.

In step 38, a function f is selected that models the numerical aperture of the non-contact detector and function Γ is computed by using Eq.(23).

In step 40, intensity $U(r_p)$ is computed using Eq.(DRBM.1) at each point $r_p$ of the surface S where $g(r_s,r_p)|_{r_p \in S}$>thresh.

In step 42, the surface flux values $J_n(r_p)$ are computed by means of Eq. (20).

In step 44, the flux J at non-contact detectors is computed using the surface flux values $J_n(r_p)$ in Eq. (23) and (24).

In step 46, intensity $U(r_d)$ is computed at non-contact detectors by using $U(r_d)=C_{nd}J(r_d)$, where now $C_{nd}$ is defined for the detector/non-diffusive medium interface according to Eq. (8). Then the control is passed back to step 28.

When all $N_{det}$ detectors were used for each of $N_{src}$ sources, control is passed to step 48. In step 48, values of the average intensity $U(r_s,r_d)$ for all $N_{src}$ sources and $N_{det}$ detectors is provided to a processor, programmed to process intensity values into a tomographic image and output the image to an I/O device.

It will be appreciated by one skilled in the art that the computational methods of the present invention can be applied both to contact and non-contact measurements of any diffuse or diffuse-like medium from many different optical tomographic imaging system configurations.

While this invention has been particularly shown and described with references to preferred embodiments thereof, it will be understood by those skilled in the art that various changes in form and details may be made therein without departing from the scope of the invention encompassed by the appended claims.

It will be apparent to those of ordinary skill in the art that methods disclosed herein may be embodied in a computer program product that includes a computer usable medium. For example, such a computer usable medium can include a readable memory device, such as a hard drive device, a CD-ROM, a DVD-ROM, or a computer diskette, having computer readable program code segments stored thereon. The computer readable medium can also include a communications or transmission medium, such as a bus or a communications link, either optical, wired, or wireless, having program code segments carried thereon as digital or analog data signals.

What is claimed is:

1. A method for real-time Diffusive Optical tomographic (DOT) imaging of a diffusive medium comprising:
   (a) directing light waves into a diffusive medium having a boundary S;
   (b) using a detector to detect an intensity of light waves emitted from the diffusive medium by using non-contact measurements of the light waves outside the diffusive medium, where there is a non-diffusive medium between the detector and the diffusive medium, wherein the diffusive medium comprises biological tissue and the non-diffusive medium comprises air, wherein the diffusive medium fills an object of volume V, bounded by the boundary surface S, wherein the volume V is of arbitrary geometry; and
   (c) processing the detected intensity to generate a tomographic image by modeling propagation of diffuse photon waves inside the arbitrarily shaped diffusive volume V taking into account the boundary surface S and modeling intensity at the non-contact detector.

2. The method of claim 1 wherein step (c) includes representing the contribution of each wave into the detected intensity as a sum of an arbitrary integer number N of terms in a series.

3. The method of claim 2 wherein each term in the series is an intensity of a wave reflected from an arbitrary surface within or outside the diffusive medium.

4. The method of claim 3, wherein step (c) further comprises:
   monitoring a gradient of the boundary surface to detect complex boundaries; and
   automatically increasing a density of local surface discretization and the number N of terms in a series, if the boundary is complex.

5. The method of claim 3, wherein step (c) further comprises: monitoring relative change in a value of the calculated intensity added by each term of the series; and
   truncating the series by selecting a finite number N of terms in a series, when the relative change in a value of the calculated intensity meets convergence criteria.

6. The method of claim 1, wherein step (c) further comprises: monitoring the gradient of a surface boundary to detect complex boundaries; automatically increasing a density of local surface discretization and the number N of terms in a series, if the boundary is complex; and optimizing an evolution step τ by assigning a value, of about $\tau = 2\,\text{imag}\{\kappa\}/\sqrt{W}+1$, wherein W is a mean diameter of the diffusive medium.

7. The method of claim 1 further including a step of selecting a tomographic imaging method, wherein the tomographic imaging method is selected from the group consisting of diffuse optical tomography, fluorescence-mediated tomography, near-field optical tomography and thermal tomography.

8. The method of claim 1, wherein the light waves are continuous wave (CW), time-resolved (TR), intensity modulated (IM) or a combination thereof.

9. The method of claim 1, wherein the light waves are near-infrared or infrared light.

10. The method of claim 1, wherein the diffusive medium is an object, and wherein the method comprises:
    administering to the object a fluorescent imaging probe; and
    detecting fluorescent light emitted from multiple points from the object, wherein the tomographic image indicates quantity of fluorescent imaging probe in a three-dimensional target region within the object.

11. The method of claim 1, wherein step (c) comprises using a Green's function to model propagation of the waves inside the diffusive medium.

12. The method of claim 1, wherein step (c) comprises using a Kirchhoff approximation to model propagation of the waves inside the diffusive medium.

13. The method of claim 1, wherein step (c) comprises using an N-order Diffuse Reflection Boundary Method (DRBM) to model propagation of waves inside the diffusive medium.

* * * * *